(12) United States Patent
Montgomery et al.

(10) Patent No.: US 11,219,376 B2
(45) Date of Patent: Jan. 11, 2022

(54) IDENTIFYING ANOMALOUS AUTOREGULATION STATE VALUES

(71) Applicant: Covidien LP, Mansfield, MA (US)

(72) Inventors: Dean Montgomery, Edinburgh (GB); Paul S. Addison, Edinburgh (GB); Andre Antunes, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 452 days.

(21) Appl. No.: 16/169,794

(22) Filed: Oct. 24, 2018

(65) Prior Publication Data

US 2020/0129076 A1    Apr. 30, 2020

(51) Int. Cl.
| A61B 5/021 | (2006.01) |
| A61B 5/00 | (2006.01) |
| A61B 5/145 | (2006.01) |

(52) U.S. Cl.
CPC .......... *A61B 5/021* (2013.01); *A61B 5/14542* (2013.01); *A61B 5/7225* (2013.01); *A61B 5/742* (2013.01)

(58) Field of Classification Search
CPC ....... A61B 5/021; A61B 5/742; A61B 5/7225; A61B 5/14542; A61B 5/746; A61B 5/026; A61B 5/4064; A61B 5/7246; A61B 5/14551
See application file for complete search history.

(56) References Cited

U.S. PATENT DOCUMENTS

| 5,743,267 | A  | 4/1998 | Nikolic et al. |
| 6,599,251 | B2 | 7/2003 | Chen et al. |
| 6,689,069 | B2 | 2/2004 | Bratteli et al. |
| 7,070,566 | B2 | 7/2006 | Medero et al. |
| 7,927,283 | B2 | 4/2011 | Riobo et al. |
| 8,366,627 | B2 | 2/2013 | Kashif et al. |

(Continued)

FOREIGN PATENT DOCUMENTS

WO    2017001023 A1    1/2017

OTHER PUBLICATIONS

Chuan et al., "Is Cerebrovascular Autoregulation Associated with Outcomes After Major Noncardiac Surgery? A Prospective Observational Pilot Study," Acta Anaesthesiologica Scandinavica, Jul. 11, 2018, 10 pp.

(Continued)

*Primary Examiner* — Devin B Henson
*Assistant Examiner* — Joseph A Tombers
(74) *Attorney, Agent, or Firm* — Shumaker & Sieffert, P.A.

(57) ABSTRACT

In some examples, a device includes sensing circuitry configured to receive one or more signals from a patient and processing circuitry configured to determine a plurality of autoregulation state values associated with a plurality of blood pressure values based on the one or more signals. The processing circuitry is further configured to determine that a first autoregulation state value of the plurality of autoregulation state values is anomalous based on other autoregulation state values of the plurality of autoregulation state values. The processing circuitry is also configured to modify the first autoregulation state value in response to determining that the first autoregulation state value is anomalous and determine an autoregulation status of the patient based on the plurality of autoregulation state values including the modified first autoregulation state value.

20 Claims, 8 Drawing Sheets

| BLOOD PRESSURE VALUE | AUTOREG. STATE VALUE |
|---|---|
| 40 mmHg | IMPAIRED |
| 45 mmHg | IMPAIRED |
| 50 mmHg | IMPAIRED |
| 55 mmHg | INTACT |
| 60 mmHg | INTACT |
| 65 mmHg | UNCATEG. |
| 70 mmHg | UNCATEG. |
| 75 mmHg | INTACT |

(56) References Cited

U.S. PATENT DOCUMENTS

| | | |
|---|---|---|
| 8,702,604 B2 | 4/2014 | Karamanoglu et al. |
| 9,474,451 B2 | 10/2016 | Brady et al. |
| 9,861,317 B2 | 1/2018 | Ochs |
| 2005/0015009 A1* | 1/2005 | Mourad ............... A61B 5/7267 600/438 |
| 2009/0326386 A1 | 12/2009 | Sethi et al. |
| 2011/0105912 A1* | 5/2011 | Widman ............... A61B 5/021 600/483 |
| 2011/0201911 A1* | 8/2011 | Johnson .................. G06F 3/041 600/365 |
| 2016/0242700 A1* | 8/2016 | Ferber .................. A61B 5/7278 |
| 2016/0367197 A1 | 12/2016 | Addison et al. |
| 2017/0095161 A1 | 4/2017 | Addison et al. |
| 2017/0105631 A1* | 4/2017 | Addison ............ A61B 5/14553 |
| 2017/0105671 A1 | 4/2017 | Borgos |
| 2017/0196501 A1* | 7/2017 | Watson ............... A61B 5/0476 |
| 2018/0014791 A1 | 1/2018 | Montgomery et al. |
| 2018/0020991 A1 | 1/2018 | Aung et al. |
| 2018/0049649 A1 | 2/2018 | Addison et al. |
| 2018/0249916 A1 | 9/2018 | Bienek et al. |
| 2018/0338731 A1 | 11/2018 | Addison et al. |

OTHER PUBLICATIONS

Tsalach et al., "Cerebral Autoregulation Real-Time Monitoring," PLoS ONE vol. 11, No. 8, Aug. 29, 2016, 27 pp.
Scheeran et al., "Journal of Clinical Monitoring and Computing 2016 End of Year Summary: Monitoring Cerebral Oxygenation and Autoregulation," Springer Science and Business Media, Jan. 2017, pp. 241-246.
U.S. Appl. No. 15/962,486, filed Apr. 25, 2018, by Montgomery.
U.S. Appl. No. 16/184,638, filed Nov. 8, 2018, by Addison.

\* cited by examiner

FIG. 6A

| BLOOD PRESSURE VALUE | AUTOREG. STATE VALUE |
|---|---|
| 40 mmHg | IMPAIRED |
| 45 mmHg | IMPAIRED |
| 50 mmHg | IMPAIRED |
| 55 mmHg | INTACT |
| 60 mmHg | INTACT |
| 65 mmHg | UNCATEG. |
| 70 mmHg | UNCATEG. |
| 75 mmHg | INTACT |

FIG. 6B

| BLOOD PRESSURE VALUE | AUTOREG. STATE VALUE |
|---|---|
| 40 mmHg | IMPAIRED |
| 45 mmHg | IMPAIRED |
| 50 mmHg | IMPAIRED |
| 55 mmHg | IMPAIRED |
| 60 mmHg | INTACT |
| 65 mmHg | UNCATEG. |
| 70 mmHg | UNCATEG. |
| 75 mmHg | INTACT |

FIG. 6C

| BLOOD PRESSURE VALUE | AUTOREG. STATE VALUE |
|---|---|
| 40 mmHg | IMPAIRED |
| 45 mmHg | IMPAIRED |
| 50 mmHg | IMPAIRED |
| 55 mmHg | IMPAIRED |
| 60 mmHg | INTACT |
| 65 mmHg | UNCATEG. |
| 70 mmHg | UNCATEG. |
| 75 mmHg | INTACT |

FIG. 6D

| BLOOD PRESSURE VALUE | AUTOREG. STATE VALUE |
|---|---|
| 40 mmHg | IMPAIRED |
| 45 mmHg | IMPAIRED |
| 50 mmHg | IMPAIRED |
| 55 mmHg | IMPAIRED |
| 60 mmHg | INTACT |
| 65 mmHg | INTACT |
| 70 mmHg | UNCATEG. |
| 75 mmHg | INTACT |

IDENTIFYING ANOMALOUS AUTOREGULATION STATE VALUES

TECHNICAL FIELD

This disclosure relates to physiological parameter monitoring.

BACKGROUND

Cerebral autoregulation (CA) is the response mechanism by which an organism regulates cerebral blood flow over a wide range of systemic blood pressure changes through complex myogenic, neurogenic, and metabolic mechanisms. Autoregulation dysfunction may result from a number of causes including, stroke, traumatic brain injury, brain lesions, brain asphyxia, or infections of the central nervous system. Intact cerebral autoregulation function occurs over a range of blood pressures defined between a lower limit of autoregulation (LLA) and an upper limit of autoregulation (ULA).

SUMMARY

This disclosure describes devices, systems, and techniques including processing circuitry configured to determine multiple autoregulation state values, where each autoregulation state value is associated with a blood pressure value, based on one or more signals received from a patient. The processing circuitry may be configured to determine that a first autoregulation state value is anomalous based on other autoregulation state values. The processing circuitry can modify the first autoregulation state value in response to determining that the first autoregulation state value is anomalous.

Clause 1: In some examples, a method includes receiving, by processing circuitry, one or more signals from a patient. The method also includes determining, by the processing circuitry, a plurality of autoregulation state values associated with a plurality of blood pressure values based on the one or more signals. The method further includes determining, by the processing circuitry, that a first autoregulation state value of the plurality of autoregulation state values is anomalous based on other autoregulation state values of the plurality of autoregulation state values. The method includes modifying, by the processing circuitry, the first autoregulation state value in response to determining that the first autoregulation state value is anomalous. The method further includes determining, by the processing circuitry, an autoregulation status of the patient based on the plurality of autoregulation state values including the modified first autoregulation state value.

Clause 2: In some examples of clause 1, determining that the first autoregulation state value is anomalous includes identifying a set of intact autoregulation state values of the plurality of autoregulation state values, each of the intact autoregulation state values of the set representing an intact autoregulation state. Determining that the first autoregulation state value is anomalous also includes determining that the first autoregulation state value represents an intact autoregulation state and determining that a difference between a blood pressure value associated with the first autoregulation state value and each of a set of blood pressure values associated with the set of intact autoregulation state values is greater than a threshold value.

Clause 3: In some examples of any of clauses 1-2, determining that the first autoregulation state value is anomalous includes determining a limit of autoregulation based on the plurality of autoregulation state values, determining that the first autoregulation state value represents an intact autoregulation state, and determining that the first autoregulation state value is outside of the limit of autoregulation.

Clause 4: In some examples of clause 3, determining the limit of autoregulation includes determining a lower limit of autoregulation based on the plurality of autoregulation state values. Determining that the first autoregulation state value is outside of the limit of autoregulation includes determining that a blood pressure value associated with the first autoregulation state value is lower than the lower limit of autoregulation.

Clause 5: In some examples of clause 3 or clause 4, determining the limit of autoregulation includes determining an upper limit of autoregulation based on the plurality of autoregulation state values. Determining that the first autoregulation state value is outside of the limit of autoregulation includes determining that a blood pressure value associated with the first autoregulation state value is higher than the upper limit of autoregulation.

Clause 6: In some examples of any of clauses 2-5, modifying the first autoregulation state value includes setting the first autoregulation state value to a value representing an impaired autoregulation state.

Clause 7: In some examples of any of clauses 1-6, determining that the first autoregulation state value is anomalous includes identifying a first set of impaired autoregulation state values of the plurality of autoregulation state values, each of the impaired autoregulation state values of the set representing an impaired autoregulation state. Determining that the first autoregulation state value represents an impaired autoregulation state, and determining that a difference between a blood pressure value associated with the first autoregulation state value and each of a set of blood pressure values associated with the set of impaired autoregulation state values is greater than a threshold value.

Clause 8: In some examples of any of clauses 1-7, determining that the first autoregulation state value is anomalous includes determining a limit of autoregulation based on the plurality of autoregulation state values, determining that the first autoregulation state value represents an impaired autoregulation state, and determining that the first autoregulation state value is inside of the limit of autoregulation.

Clause 9: In some examples of clause 8, determining the limit of autoregulation includes determining a lower limit of autoregulation based on the plurality of autoregulation state values. Determining that the first autoregulation state value is inside of the limit of autoregulation includes determining that a blood pressure value associated with the first autoregulation state value is higher than the lower limit of autoregulation.

Clause 10: In some examples of clause 8 or clause 9, determining the limit of autoregulation includes determining an upper limit of autoregulation based on the plurality of autoregulation state values. Determining that the first autoregulation state value is inside of the limit of autoregulation includes determining that a blood pressure value associated with the first autoregulation state value is lower than the upper limit of autoregulation.

Clause 11: In some examples of any of clauses 7-10, modifying the first autoregulation state value includes setting the first autoregulation state value to a value representing an intact autoregulation state.

Clause 12: In some examples of any of clauses 1-11, determining that the first autoregulation state value is anomalous includes determining that the first autoregulation state value represents an uncategorized autoregulation state. Determining that the first autoregulation state value is anomalous also includes determining that a first set of autoregulation state values of the plurality of autoregulation state values has a categorized autoregulation value, the categorized autoregulation value representing a categorized autoregulation state, where the categorized autoregulation value includes an intact autoregulation value or an impaired autoregulation value, and where the first set of autoregulation state values is associated with blood pressure values that are higher than a blood pressure value associated with the first autoregulation state value. Determining that the first autoregulation state value is anomalous further includes determining that a second set of autoregulation state values of the plurality of autoregulation state values has the categorized autoregulation value, where the second set of autoregulation state values is associated with blood pressure values that are lower than a blood pressure value associated with the first autoregulation state value. Modifying the first autoregulation state value includes setting the first autoregulation state value to the categorized value.

Clause 13: In some examples of clause 12, determining that the first autoregulation state value is anomalous further includes determining that a difference between each of the blood pressure values associated with the first set of autoregulation state values and the blood pressure value associated with the first autoregulation state value is less than a threshold value. Determining that the first autoregulation state value is anomalous also includes determining that a difference between each of the blood pressure values associated with the second set of autoregulation state values and the blood pressure value associated with the first autoregulation state value is less than the threshold value.

Clause 14: In some examples of clause 12 or clause 13, the method further includes determining that each autoregulation state value of a set of consecutive autoregulation state values has an uncategorized autoregulation value, where the set of consecutive autoregulation state values is associated with consecutive blood pressure values that span less than ten millimeters of mercury. The method also includes determining that the set of consecutive autoregulation state values including the first autoregulation state value is anomalous.

Clause 15: In some examples of any of clauses 1-14, the first autoregulation state value is associated with a first blood pressure value, and determining that the first autoregulation state value is anomalous includes applying a smoothing function to the plurality of autoregulation state values to generate a plurality of smoothed autoregulation state values. Determining that the first autoregulation state value is anomalous also includes determining that a first smoothed autoregulation state value of the plurality of smoothed autoregulation state values and the first autoregulation state value have different values, where the first smoothed autoregulation state value is associated with the first blood pressure value. Modifying the first autoregulation state value includes setting the first autoregulation state value to the first smoothed autoregulation state value in response to determining that the first smoothed autoregulation state value and the first autoregulation state value have different values.

Clause 16: In some examples of clause 15, applying the smoothing function includes applying a Gaussian filter to the plurality of autoregulation state values to generate the plurality of smoothed autoregulation state values.

Clause 17: In some examples of any of clauses 1-16, the first autoregulation state value is associated with a first blood pressure value, where the method further includes determining a confidence metric for autoregulation state values associated with blood pressure values within a threshold value from the first blood pressure value, where the autoregulation state values associated with the blood pressure values within the threshold value from the first blood pressure value have a predominant autoregulation value. The method also includes determining that the confidence metric is greater than a threshold confidence level. Modifying the first autoregulation state value includes setting the first autoregulation state value to the predominant autoregulation value in response to determining that the confidence metric is greater than the threshold confidence level.

Clause 18: In some examples of any of clauses 1-17, the first autoregulation state value is associated with a first blood pressure value, where the method further includes determining a confidence metric for autoregulation state values associated with blood pressure values within a threshold value from the first blood pressure value. The method includes determining that the confidence metric is less than a threshold confidence level. Modifying the first autoregulation state value includes setting the first autoregulation state value to an uncategorized autoregulation value in response to determining that the confidence metric is less than the threshold confidence level, the uncategorized autoregulation value representing an uncategorized autoregulation state.

Clause 19: In some examples of any of clauses 1-18, the method further includes storing an unmodified value of the first autoregulation state value and determining new autoregulation state values for the plurality of autoregulation state values after modifying the first autoregulation state value and based on the unmodified value of the first autoregulation state value.

Clause 20: In some examples of any of clauses 1-19, the method further includes applying an expected autoregulation function to the plurality of autoregulation state values to generate a modified plurality of autoregulation state values. The expected autoregulation function includes a lower limit of autoregulation, an upper limit of autoregulation, a first set of autoregulation state values representing an intact autoregulation state between the lower limit of autoregulation and the upper limit of autoregulation, a second set of autoregulation state values representing an intact autoregulation state associated with blood pressure values less than the lower limit of autoregulation, and a third set of autoregulation state values representing an intact autoregulation state associated with blood pressure values greater than the upper limit of autoregulation.

Clause 21: In some examples of clause 20, the method further includes determining the expected autoregulation function based on a previous morphology of the plurality of autoregulation state values.

Clause 22: In some examples of clause 20 or clause 21, the method further includes determining the expected autoregulation function based on a fit of historical patient blood pressure value data.

Clause 23: In some examples of any of clauses 1-22, the method further includes determining a current blood pressure value for the patient based on the one or more signals and setting a second autoregulation state value of the plurality of autoregulation state values, where the second autoregulation state value is associated with the current blood pressure value.

Clause 24: In some examples, a device includes sensing circuitry configured to receive one or more signals from a patient and processing circuitry configured to determine a plurality of autoregulation state values associated with a plurality of blood pressure values based on the one or more signals. The processing circuitry is also configured to determine that a first autoregulation state value of the plurality of autoregulation state values is anomalous based on other autoregulation state values of the plurality of autoregulation state values. The processing circuitry is further configured to modify the first autoregulation state value in response to determining that the first autoregulation state value is anomalous. The processing circuitry is configured to determine an autoregulation status of the patient based on the plurality of autoregulation state values including the modified first autoregulation state value.

Clause 25: In some examples of clause 24, the processing circuitry is configured to perform the method of examples 1-23 or any combination thereof.

Clause 26: In some examples of clause 24 or clause 25, the processing circuitry is configured to determine that the first autoregulation state value is anomalous at least in part by identifying a set of intact autoregulation state values of the plurality of autoregulation state values, each of the intact autoregulation state values of the set representing an intact autoregulation state, determining that the first autoregulation state value represents an intact autoregulation state, and determining that a difference between a blood pressure value associated with the first autoregulation state value and each of a set of blood pressure values associated with the set of intact autoregulation state values is greater than a threshold value.

Clause 27: In some examples of any of clause 25-26, the processing circuitry is configured to determine that the first autoregulation state value is anomalous at least in part by determining a limit of autoregulation based on the plurality of autoregulation state values, determining that the first autoregulation state value represents an intact autoregulation state, and determining that the first autoregulation state value is outside of the limit of autoregulation.

Clause 28: In some examples of clause 27, the processing circuitry is configured to determine the limit of autoregulation at least in part by determining a lower limit of autoregulation based on the plurality of autoregulation state values. The processing circuitry is configured to determine that the first autoregulation state value is outside of the limit of autoregulation at least in part by determining that a blood pressure value associated with the first autoregulation state value is lower than the lower limit of autoregulation.

Clause 29: In some examples of clause 27 or clause 28, the processing circuitry is configured to determine the limit of autoregulation at least in part by determining an upper limit of autoregulation based on the plurality of autoregulation state values. The processing circuitry is configured to determine that the first autoregulation state value is outside of the limit of autoregulation at least in part by determining that a blood pressure value associated with the first autoregulation state value is higher than the upper limit of autoregulation.

Clause 30: In some examples of any of clauses 26-29, the processing circuitry is configured to modify the first autoregulation state value at least in part by setting the first autoregulation state value to a value representing an impaired autoregulation state.

Clause 31: In some examples of any of clauses 24-30, the processing circuitry is configured to determine that the first autoregulation state value is anomalous at least in part by identifying a first set of impaired autoregulation state values of the plurality of autoregulation state values, each of the impaired autoregulation state values of the set representing an impaired autoregulation state, determining that the first autoregulation state value represents an impaired autoregulation state, and determining that a difference between a blood pressure value associated with the first autoregulation state value and each of a set of blood pressure values associated with the set of impaired autoregulation state values is greater than a threshold value.

Clause 32: In some examples of any of clauses 24-31, the processing circuitry is configured to determine that the first autoregulation state value is anomalous at least in part by determining a limit of autoregulation based on the plurality of autoregulation state values, determining that the first autoregulation state value represents an impaired autoregulation state, and determining that the first autoregulation state value is inside of the limit of autoregulation.

Clause 33: In some examples of clause 32, the processing circuitry is configured to determine the limit of autoregulation at least in part by determining a lower limit of autoregulation based on the plurality of autoregulation state values. The processing circuitry is configured to determine that the first autoregulation state value is inside of the limit of autoregulation at least in part by determining that a blood pressure value associated with the first autoregulation state value is higher than the lower limit of autoregulation.

Clause 34: In some examples of clause 32 or clause 33, the processing circuitry is configured to determine the limit of autoregulation at least in part determining an upper limit of autoregulation based on the plurality of autoregulation state values. The processing circuitry is configured to determine that the first autoregulation state value is inside of the limit of autoregulation at least in part determining that a blood pressure value associated with the first autoregulation state value is lower than the upper limit of autoregulation.

Clause 35: In some examples of any of clauses 31-34, the processing circuitry is configured to modify the first autoregulation state value at least in part setting the first autoregulation state value to a value representing an intact autoregulation state.

Clause 36: In some examples of any of clauses 24-35, the processing circuitry is configured to determine that the first autoregulation state value is anomalous at least in part determining that the first autoregulation state value represents an uncategorized autoregulation state, determining that a first set of autoregulation state values of the plurality of autoregulation state values has a categorized autoregulation value, the categorized autoregulation value representing a categorized autoregulation state, where the categorized autoregulation value at least in part an intact autoregulation value or an impaired autoregulation value, and where the first set of autoregulation state values is associated with blood pressure values that are higher than a blood pressure value associated with the first autoregulation state value. The processing circuitry is configured to determine that the first autoregulation state value is anomalous at least in part determining that a second set of autoregulation state values of the plurality of autoregulation state values has the categorized autoregulation value, where the second set of autoregulation state values is associated with blood pressure values that are lower than a blood pressure value associated with the first autoregulation state value. The processing circuitry is configured to modify the first autoregulation state value at least in part setting the first autoregulation state value to the categorized value.

Clause 37: In some examples of clause 36, the processing circuitry is configured to determine that the first autoregulation state value is anomalous further at least in part determining that a difference between each of the blood pressure values associated with the first set of autoregulation state values and the blood pressure value associated with the first autoregulation state value is less than a threshold value and determining that a difference between each of the blood pressure values associated with the second set of autoregulation state values and the blood pressure value associated with the first autoregulation state value is less than the threshold value.

Clause 38: In some examples of clause 36 or clause 37, the processing circuitry is further configured to determine that each autoregulation state value of a set of consecutive autoregulation state values has an uncategorized autoregulation value, where the set of consecutive autoregulation state values is associated with consecutive blood pressure values that span less than ten millimeters of mercury. The processing circuitry is also configured to determine that the set of consecutive autoregulation state values including the first autoregulation state value is anomalous.

Clause 39: In some examples of any of clauses 24-38, the first autoregulation state value is associated with a first blood pressure value, and the processing circuitry is configured to determine that the first autoregulation state value is anomalous at least in part applying a smoothing function to the plurality of autoregulation state values to generate a plurality of smoothed autoregulation state values and determining that the first autoregulation state value is anomalous also includes determining that a first smoothed autoregulation state value of the plurality of smoothed autoregulation state values and the first autoregulation state value have different values, where the first smoothed autoregulation state value is associated with the first blood pressure value. The processing circuitry is configured to modify the first autoregulation state value at least in part setting the first autoregulation state value to the first smoothed autoregulation state value in response to determining that the first smoothed autoregulation state value and the first autoregulation state value have different values.

Clause 40: In some examples of clause 39, the processing circuitry is configured to determine apply the smoothing function at least in part applying a Gaussian filter to the plurality of autoregulation state values to generate the plurality of smoothed autoregulation state values.

Clause 41: In some examples of any of clauses 24-40, the first autoregulation state value is associated with a first blood pressure value, and the processing circuitry is further configured to determine a confidence metric for autoregulation state values associated with blood pressure values within a threshold value from the first blood pressure value, where the autoregulation state values associated with the blood pressure values within the threshold value from the first blood pressure value have a predominant autoregulation value. The processing circuitry is also configured to determine that the confidence metric is greater than a threshold confidence level. The processing circuitry is configured to modify the first autoregulation state value at least in part setting the first autoregulation state value to the predominant autoregulation value in response to determining that the confidence metric is greater than the threshold confidence level.

Clause 42: In some examples of any of clauses 24-41, the first autoregulation state value is associated with a first blood pressure value, and the processing circuitry is further configured to determine a confidence metric for autoregulation state values associated with blood pressure values within a threshold value from the first blood pressure value. The processing circuitry is also configured to determine that the confidence metric is less than a threshold confidence level. The processing circuitry is configured to modify the first autoregulation state value at least in part setting the first autoregulation state value to an uncategorized autoregulation value in response to determining that the confidence metric is less than the threshold confidence level, the uncategorized autoregulation value representing an uncategorized autoregulation state.

Clause 43: In some examples of any of clauses 24-42, the processing circuitry is further configured to store an unmodified value of the first autoregulation state value and determining new autoregulation state values for the plurality of autoregulation state values after modifying the first autoregulation state value and based on the unmodified value of the first autoregulation state value.

Clause 44: In some examples of any of clauses 24-43, the processing circuitry is further configured to apply an expected autoregulation function to the plurality of autoregulation state values to generate a modified plurality of autoregulation state values. The expected autoregulation function includes a lower limit of autoregulation, an upper limit of autoregulation, a first set of autoregulation state values representing an intact autoregulation state between the lower limit of autoregulation and the upper limit of autoregulation, a second set of autoregulation state values representing an intact autoregulation state associated with blood pressure values less than the lower limit of autoregulation, and a third set of autoregulation state values representing an intact autoregulation state associated with blood pressure values greater than the upper limit of autoregulation.

Clause 45: In some examples of clause 44, the processing circuitry is further configured to determine the expected autoregulation function based on a previous morphology of the plurality of autoregulation state values.

Clause 46: In some examples of clause 44 or clause 45, the processing circuitry is further configured to determine the expected autoregulation function based on a fit of historical patient blood pressure value data.

Clause 47: In some examples of any of clauses 24-46, the processing circuitry is further configured to determine a current blood pressure value for the patient based on the one or more signals and set a second autoregulation state value of the plurality of autoregulation state values, where the second autoregulation state value is associated with the current blood pressure value.

Clause 48: In some examples of any of clauses 24-47, the device also includes a memory, where the processing circuitry is further configured to store the plurality of autoregulation state values to the memory.

Clause 49: In some examples of any of clauses 24-48, the device also includes a memory, where the processing circuitry is further configured to present, via the display, an indication of the autoregulation status.

Clause 48: In some examples, a device includes a display, a memory, and processing circuitry configured to determine a plurality of autoregulation state values associated with a plurality of blood pressure values based on one or more signals received from a patient and store the plurality of autoregulation state values to the memory. The processing circuitry is also configured to determine that a first autoregulation state value of the plurality of autoregulation state values is anomalous based on other autoregulation state values of the plurality of autoregulation state values. The processing circuitry is further configured to modify the first autoregulation state value in response to determining that the first autoregulation state value is anomalous. The processing circuitry is configured to determine an autoregulation status of the patient based on the plurality of autoregulation state values including the modified first autoregulation state value and present, via the display, an indication of the autoregulation status.

Clause 49: In some examples of clause 48, the processing circuitry is configured to perform the method of examples 1-23 or any combination thereof.

Clause 50: In some examples, a device includes a computer-readable medium having executable instructions stored thereon, configured to be executable by processing circuitry for causing the processing circuitry to receive one or more signals from a patient and determine a plurality of autoregulation state values associated with a plurality of blood pressure values based on the one or more signals. The instructions further cause the processing circuitry to determine that a first autoregulation state value of the plurality of autoregulation state values is anomalous based on other autoregulation state values of the plurality of autoregulation state values. The instructions further cause the processing circuitry to modify the first autoregulation state value in response to determining that the first autoregulation state value is anomalous. The instructions further cause the processing circuitry to determine an autoregulation status of the patient based on the plurality of autoregulation state values including the modified first autoregulation state value.

Clause 51: In some examples of clause 50, the instructions are configured to cause the processing circuitry to perform the method of examples 1-23 or any combination thereof.

Clause 52: In some examples of clause 50 or clause 51, the instructions to determine that the first autoregulation state value is anomalous include instructions to determine a limit of autoregulation based on the plurality of autoregulation state values, determine that the first autoregulation state value represents an intact autoregulation state; and determine that the first autoregulation state value is outside of the limit of autoregulation.

Clause 53: In some examples of any of clauses 50-52, the instructions to determine that the first autoregulation state value is anomalous include instructions to determine a limit of autoregulation based on the plurality of autoregulation state values, determine that the first autoregulation state value represents an impaired autoregulation state, and determine that the first autoregulation state value is inside of the limit of autoregulation.

The details of one or more examples are set forth in the accompanying drawings and the description below. Other features, objects, and advantages will be apparent from the description and drawings, and from the claims.

BRIEF DESCRIPTION OF DRAWINGS

FIGS. 6A-6D are block diagrams illustrating example data structures storing a plurality of autoregulation state values that are updated by processing circuitry of a regional oximetry device.

DETAILED DESCRIPTION

Figure 1:
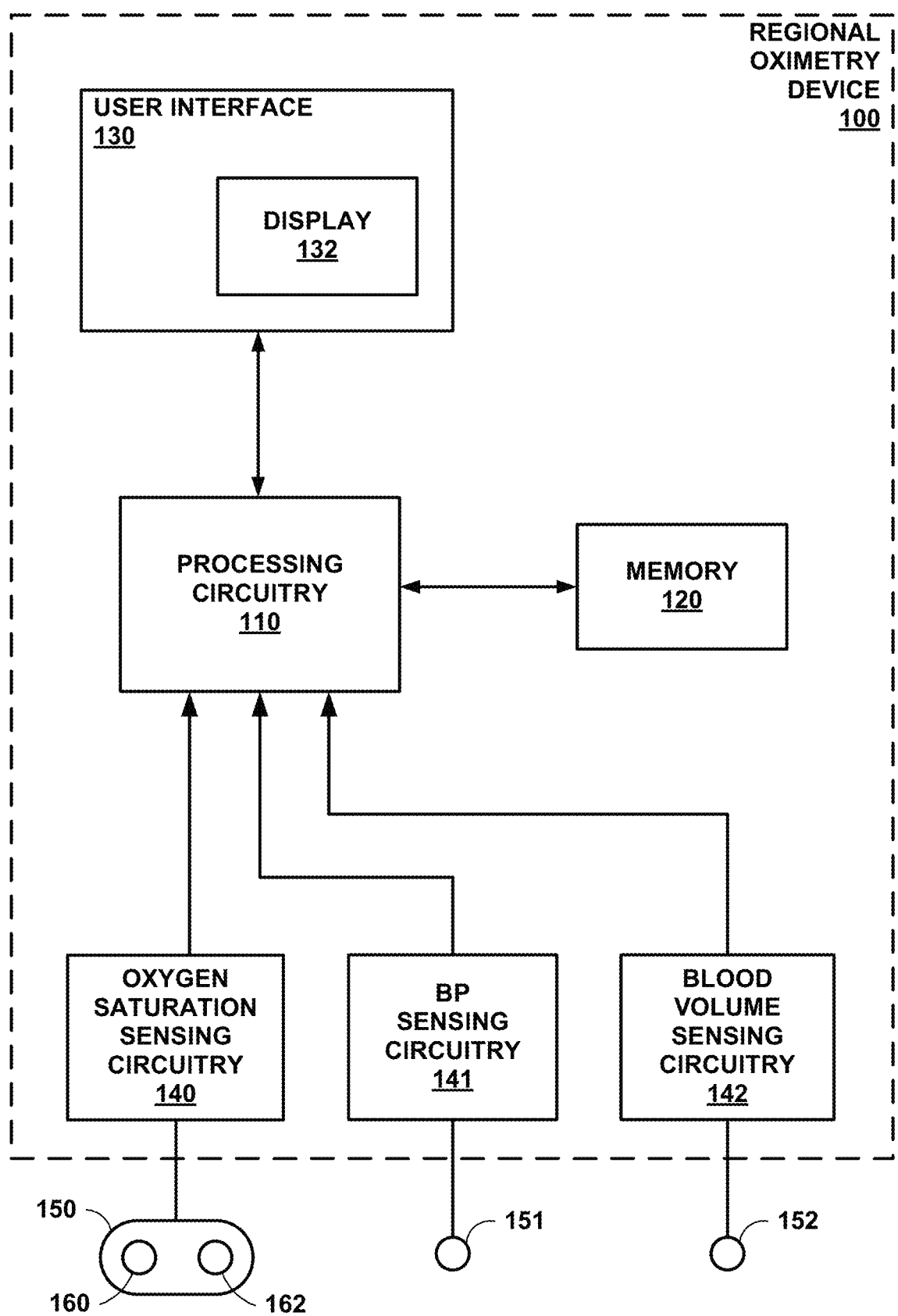
FIG. 1 is a conceptual block diagram illustrating an example regional oximetry device.

This disclosure describes devices, systems, and techniques for determining an autoregulation status of a patient based on a plurality of autoregulation state values, where each autoregulation state value is associated with a blood pressure value of the patient. Each of the plurality of autoregulation state values may be associated with a particular blood pressure value and may include a value representing an intact autoregulation state, a value representing an impaired autoregulation state, or a value representing an uncategorized autoregulation state for the particular blood pressure value. The processing circuitry may be configured to store and periodically update the plurality of autoregulation state values.

The processing circuitry may be configured to determine a current blood pressure value for a patient and determine an autoregulation state associated with the current blood pressure for the patient. The processing circuitry may then be configured to set the autoregulation state value associated with the current blood pressure value to the determined autoregulation state. As the blood pressure of the patient changes, the processing circuitry may continually or periodically determine an autoregulation state value for the then-current blood pressure value. Thus, the processing circuitry may be configured to continually (e.g., at intervals in real time) set, update, or change the autoregulation state value associated with the then-current blood pressure value.

Additional example details of determining autoregulation state values based on physiological parameters and correlation coefficients may be found in commonly assigned U.S. Patent Application Publication No. 2016/0367197 filed on Jun. 16, 2016, entitled "Systems and Methods for Reducing Signal Noise When Monitoring Autoregulation," and commonly assigned U.S. Patent Application Publication No. 2017/0105631 filed on Oct. 18, 2016, entitled "System and Method for Providing Blood Pressure Safe Zone Indication During Autoregulation Monitoring," which are incorporated herein by reference in their entirety.

In some examples, the plurality of autoregulation state values may include anomalous autoregulation state values. An example of an anomalous autoregulation state value is a value representing an impaired autoregulation state surrounding by values an intact autoregulation state. For example, the processing circuitry may be configured to determine an autoregulation state value representing an impaired autoregulation state associated with a blood pressure value of eighty millimeters of mercury, even though all of the other autoregulation state values associated with blood pressure values between sixty and one hundred millimeters of mercury are associated with an intact autoregulation state. This disclosure also describes other possible examples of anomalous autoregulation state values.

In examples in which the processing circuitry determines that a first autoregulation state value is anomalous, the processing circuitry may be configured to modify the first autoregulation state value. For example, the processing circuitry may be configured to switch the first autoregulation state value from a value representing an intact autoregulation state to a value representing an impaired autoregulation state, or vice versa, in response to that the first autoregulation state value is anomalous. In some examples, the processing circuitry is configured to set an uncategorized autoregulation value to a categorized autoregulation value, such as a value representing an intact or an impaired autoregulation state, in response to determining that the uncategorized autoregulation value is anomalous. The processing circuitry may be further configured to set a categorized autoregulation value to an uncategorized autoregulation value in response to determining that the categorized autoregulation value is anomalous.

Anomalous autoregulation state values can occur as the processing circuitry determines each value of the plurality of autoregulation state values. Some reasons for an anomalous autoregulation state value include rapid changes in patient state, electrocautery, damping of blood pressures due to catherization, changes in sensed blood pressure due to probe movement, and changes in sensed blood pressure due to line flushing, for example. A patient state, as indicated by sensed physiological signals, may change relatively rapidly over time. In response to a changing patient state, the values of a physiological parameter may change rapidly while the values of another physiological parameter may change less rapidly. Thus, correlation coefficient values associated with time periods during and just after the change in patient state may not necessarily be an accurate reflection of the new patient state.

Even if the patient state does not change, the values of a physiological parameter can change rapidly, and some or all of the rapidly changing values may not be accurate. Processing circuitry that modifies anomalous autoregulation state values can reduce the effect of the anomalous autoregulation state values, which may be less likely to be accurate. Thus, the resulting estimates of an autoregulation status of a patient by the processing circuitry may be more accurate when the processing circuitry uses the modified anomalous autoregulation state values.

The devices, systems, and techniques of this disclosure may allow for determining and presenting more accurate autoregulation state values and more accurate estimates of the autoregulation status of a patient. The presentation of more accurate and more stable information with fewer anomalies may result in increased confidence by a clinician viewing the presented information, which may lead to more informed decision making by the clinician and better patient outcomes. A clinician may lose confidence in the information presented by the processing circuitry if the information is less stable, less accurate, and/or there are more anomalies. By modifying anomalous autoregulation state values, the processing circuitry may base the determination of autoregulation status on more stable, accurate, and/or coherent autoregulation state values.

The autoregulation status of a patient may be an indication that the cerebral autoregulation control mechanism of the patient is intact (e.g., functioning properly) or impaired (e.g., not functioning properly). A cerebral autoregulation control mechanism of the body may regulate cerebral blood flow (CBF) over a range of systemic blood pressures. This range of systemic blood pressures may lie within an LLA and a ULA. Outside of the LLA and the ULA, blood pressure directly drives CBF, and cerebral autoregulation function may thus be considered impaired.

One method to determine the limits of autoregulation (e.g., the LLA and ULA) noninvasively using near-infrared spectroscopy (NIRS) technology may include the COx measure, which is a moving correlation index between mean arterial pressure (MAP) and regional oxygen saturation ($rSO_2$). The COx measure (e.g., the Pearson coefficient) is derived from the correlation between $rSO_2$ and MAP. COx relates to the regression line fit or linear correlation between $rSO_2$ and MAP over a time window having a particular length, such as three hundred seconds, in some examples. The COx method may be used to produce a representation of a patient's blood-pressure-dependent autoregulation status.

When the cerebral autoregulation is intact for a patient, there is typically no correlation between MAP and $rSO_2$. In contrast, MAP and $rSO_2$ typically directly correlate (e.g., the correlation index of COx is approximately equal to positive one) when the cerebral autoregulation is impaired. In practice, however, sensed data indicative of autoregulation may be noisy and/or there might be a slightly correlated relationship between variables (e.g., MAP and $rSO_2$) even when cerebral autoregulation is intact for the patient.

Some existing systems for monitoring autoregulation may determine a patient's autoregulation status based on various physiological parameter values (also referred to herein as physiological values). Such physiological values may be subject to various sources of error, such as noise caused by relative sensor and patient motion, operator error, poor quality measurements, drugs, or other anomalies. However, some existing systems for monitoring autoregulation may not reduce the various sources of error when utilizing the measured physiological values to determine the patient's autoregulation status. Furthermore, some existing systems may not determine and/or utilize a reliable metric to determine whether the autoregulation status calculated from the physiological values is reliable. Accordingly, the autoregulation status determined by such existing systems may be less accurate or less reliable.

In an intact region of cerebral autoregulation, there may be no correlation between these variables whereas in an impaired region of cerebral autoregulation, the correlation index should approximate unity. In practice, however, the data may be noisy and/or the intact region may exhibit a slightly positive relationship. This positive relationship may render traditional autoregulation limit calculations difficult to perform, resulting in the need for manual interpretation of the data using arbitrary thresholds. Further, the underlying mathematics of the technique may be asymmetric in terms of the results produced for impaired and intact regions and may be, in fact, not computable for the ideal case within the intact region.

A physician may monitor a patient's autoregulation through the use of various monitoring devices and systems that measure various physiological parameters. In certain aspects of the present disclosure, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) may be derived based at least in part on a linear correlation between the patient's blood pressure and oxygen saturation. In addition, in certain aspects of the present disclosure, the patient's autoregulation may be monitored by correlating measurements of the patient's blood pressure with measurements of the patient's blood volume (e.g., blood volume proxy). In particular, a hemoglobin volume index (HVx) may be derived based at least in part on a linear correlation between the patient's blood pressure and blood volume.

In some examples, various other linear correlations such as HVx may be determined to help evaluate a patient's autoregulation status. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indices may be utilized to determine or help evaluate a patient's autoregulation. The devices, systems, and techniques of this disclosure can also be applied to the determination of indices such as HVx, Mx, PRx, and/or any other indices, coefficients, and correlations. For example, processing circuitry may be configured to determine an estimate of a limit of autoregulation based on a set of HVx indices, a set of Mx indices, and/or a set of PRx indices.

In addition, processing circuitry may be configured to determine an estimate of a limit of autoregulation based on a gradients-based method. The processing circuitry can perform a gradients-based method by analyzing a relationship between a change in the patient's blood pressure and a change in the patient's oxygen saturation over a period of time. Additional example details of gradients-based methods are described in commonly assigned U.S. Patent Application Publication No. 2018/0014791 filed Jul. 13, 2017, and entitled "Systems and Methods of Monitoring Autoregulation," the entire content of which is incorporated herein by reference.

FIG. 1 is a conceptual block diagram illustrating an example regional oximetry device 100. Regional oximetry device 100 includes processing circuitry 110, memory 120, user interface 130, display 132, sensing circuitry 140-142, and sensing device(s) 150-152. In some examples, regional oximetry device 100 may be configured to determine and display the cerebral autoregulation status of a patient, e.g., during a medical procedure or for more long-term monitoring, such as fetal monitoring. A clinician may receive information regarding the cerebral autoregulation status of a patient via display 132 and adjust treatment or therapy to the patient based on the cerebral autoregulation status information.

Processing circuitry 110, as well as other processors, processing circuitry, controllers, control circuitry, and the like, described herein, may include one or more processors. Processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 110 may include multiple components, such as any combination of one or more microprocessors, one or more DSPs, one or more ASICs, or one or more FPGAs, as well as other discrete or integrated logic circuitry, and/or analog circuitry.

Memory 120 may be configured to store measurements of physiological parameters, MAP values, $rSO_2$ values, COx values, and value(s) of an LLA and/or a ULA, for example. Memory 120 may also be configured to store data such as autoregulation state values including modified and unmodified values, threshold values and rates, smoothing functions, Gaussian filters, confidence metrics, expected autoregulation functions, historical patient blood pressure value data, and/or estimates of limits of autoregulation. The threshold values and rates, smoothing functions, Gaussian filters, confidence metrics, expected autoregulation functions, and historical patient blood pressure value data may stay constant throughout the use of device 100 and across multiple patients, or these values may change over time.

In some examples, memory 120 may store program instructions, which may include one or more program modules, which are executable by processing circuitry 110. When executed by processing circuitry 110, such program instructions may cause processing circuitry 110 to provide the functionality ascribed to it herein. The program instructions may be embodied in software, firmware, and/or RAMware. Memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 130 and/or display 132 may be configured to present information to a user (e.g., a clinician). User interface 130 and/or display 132 may be configured to present a graphical user interface to a user, where each graphical user interface may include indications of values of one or more physiological parameters of a patient. For example, processing circuitry 110 may be configured to present autoregulation state values, blood pressure values, physiological parameter values, and indications of autoregulation status (e.g., cerebral autoregulation status) of a patient via display 132. In examples in which processing circuitry 110 determines that the autoregulation status of the patient is impaired, then processing circuitry 110 may present a notification (e.g., an alert) indicating the impaired cerebral autoregulation status via display 132. As another example, processing circuitry 110 may present, via display 132, estimates of $rSO_2$ for a patient, an estimate of the blood oxygen saturation ($SpO_2$) determined by processing circuitry 110, pulse rate information, respiration rate information, blood pressure, any other patient parameters, or any combination thereof.

User interface 130 and/or display 132 may include a monitor, cathode ray tube display, a flat panel display such as a liquid crystal (LCD) display, a plasma display, a light emitting diode (LED) display, and/or any other suitable display. User interface 130 and/or display 132 may be part of a personal digital assistant, mobile phone, tablet computer, laptop computer, any other suitable computing device, or any combination thereof, with a built-in display or a separate display. User interface 130 may also include means for projecting audio to a user, such as speaker(s). Processing circuitry 110 may be configured to present, via user interface 130, a visual, audible, tactile, or somatosensory notification (e.g., an alarm signal) indicative of the patient's autoregulation status and/or a notification indicative of the patient's limit(s) of autoregulation.

User interface 130 may include or be part of any suitable device for conveying such information, including a computer workstation, a server, a desktop, a notebook, a laptop, a handheld computer, a mobile device, or the like. In some examples, processing circuitry 110 and user interface 130 may be part of the same device or supported within one housing (e.g., a computer or monitor). In other examples, processing circuitry 110 and user interface 130 may be separate devices configured to communicate through a wired connection or a wireless connection (e.g., communication interface 290 shown in FIG. 2).

Sensing circuitry 140-142 may be configured to receive physiological signals sensed by respective sensing device(s) 150-152 and communicate the physiological signals to processing circuitry 110. Sensing device(s) 150-152 may include any sensing hardware configured to sense a physiological parameter of a patient, such as, but not limited to, one or more electrodes, optical receivers, blood pressure cuffs, or the like. Sensing circuitry 140-142 may convert the physiological signals to usable signals for processing circuitry 110, such that processing circuitry 110 is configured to receive signals generated by sensing circuitry 140-142. Sensing circuitry 140-142 may receive signals indicating physiological parameters from a patient, such as, but not limited to, blood pressure, regional oxygen saturation, blood volume, heart rate, and respiration. Sensing circuitry 140-142 may include, but are not limited to, blood pressure sensing circuitry, oxygen saturation sensing circuitry, blood volume sensing circuitry, heart rate sensing circuitry, temperature sensing circuitry, electrocardiography (ECG) sensing circuitry, electroencephalogram (EEG) sensing circuitry, or any combination thereof. In some examples, sensing circuitry 140-142 and/or processing circuitry 110 may include signal processing circuitry such as an analog-to-digital converter.

In some examples, oxygen saturation sensing device 150 is a regional oxygen saturation sensor configured to generate an oxygen saturation signal indicative of blood oxygen saturation within the venous, arterial, and/or capillary systems within a region of the patient. For example, oxygen saturation sensing device 150 may be configured to be placed on the patient's forehead and may be used to determine the oxygen saturation of the patient's blood within the venous, arterial, and/or capillary systems of a region underlying the patient's forehead (e.g., in the cerebral cortex).

In such cases, oxygen saturation sensing device 150 may include emitter 160 and detector 162. Emitter 160 may include at least two light emitting diodes (LEDs), each configured to emit at different wavelengths of light, e.g., red or near infrared light. In some examples, light drive circuitry (e.g., within sensing device 150, sensing circuitry 140, and/or processing circuitry 110) may provide a light drive signal to drive emitter 160 and to cause emitter 160 to emit light. In some examples, the LEDs of emitter 160 emit light in the wavelength range of about 600 nanometers (nm) to about 1000 nm. In a particular example, one LED of emitter 160 is configured to emit light at a wavelength of about 730 nm and the other LED of emitter 160 is configured to emit light at a wavelength of about 810 nm. Other wavelengths of light may also be used in other examples.

Detector 162 may include a first detection element positioned relatively "close" (e.g., proximal) to emitter 160 and a second detection element positioned relatively "far" (e.g., distal) from emitter 160. Light intensity of multiple wavelengths may be received at both the "close" and the "far" detector 162. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation signal for the target tissues over time. Oxygen saturation sensing device 150 may provide the regional oxygen saturation signal to processing circuitry 110 or to any other suitable processing device to enable evaluation of the patient's autoregulation status.

In operation, blood pressure sensing device 151 and oxygen saturation sensing device 150 may each be placed on the same or different parts of the patient's body. For example, blood pressure sensing device 151 and oxygen saturation sensing device 150 may be physically separate from each other and may be separately placed on the patient. As another example, blood pressure sensing device 151 and oxygen saturation sensing device 150 may in some cases be part of the same sensor or supported by a single sensor housing. For example, blood pressure sensing device 151 and oxygen saturation sensing device 150 may be part of an integrated oximetry system configured to non-invasively measure blood pressure (e.g., based on time delays in a PPG signal) and regional oxygen saturation. One or both of blood pressure sensing device 151 or oxygen saturation sensing device 150 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an example regional oximetry device 100 is shown in FIG. 1, the components illustrated in FIG. 1 are not intended to be limiting. Additional or alternative components and/or implementations may be used in other examples.

Blood pressure sensing device 151 may be any sensor or device configured to obtain the patient's blood pressure (e.g., arterial blood pressure). For example, blood pressure sensing device 151 may include a blood pressure cuff for non-invasively monitoring blood pressure or an arterial line for invasively monitoring blood pressure. In certain examples, blood pressure sensing device 151 may include one or more pulse oximetry sensors. In some such cases, the patient's blood pressure may be derived by processing time delays between two or more characteristic points within a single plethysmography (PPG) signal obtained from a single pulse oximetry sensor.

Additional example details of deriving blood pressure based on a comparison of time delays between certain components of a single PPG signal obtained from a single pulse oximetry sensor are described in commonly assigned U.S. Patent Application Publication No. 2009/0326386 filed Sep. 30, 2008, and entitled "Systems and Methods for Non-Invasive Blood Pressure Monitoring," the entire content of which is incorporated herein by reference. In other cases, the patient's blood pressure may be continuously, non-invasively monitored via multiple pulse oximetry sensors placed at multiple locations on the patient's body. As described in commonly assigned U.S. Pat. No. 6,599,251, entitled "Continuous Non-invasive Blood Pressure Monitoring Method and Apparatus," the entire content of which is incorporated herein by reference, multiple PPG signals may be obtained from the multiple pulse oximetry sensors, and the PPG signals may be compared against one another to estimate the patient's blood pressure. Regardless of its form, blood pressure sensing device 151 may be configured to generate a blood pressure signal indicative of the patient's blood pressure (e.g., arterial blood pressure) over time. Blood pressure sensing device 151 may provide the blood pressure signal to sensing circuitry 141, processing circuitry 110, or to any other suitable processing device to enable evaluation of the patient's autoregulation status.

Processing circuitry 110 may be configured to receive one or more signals generated by sensing devices 150-152 and sensing circuitry 140-142. The signals may include a signal indicating blood pressure, a signal indicating oxygen saturation, and/or a signal indicating blood volume of a patient (e.g., an isosbestic signal). Processing circuitry 110 may be configured to determine values of physiological parameters based on the two or more signals received by sensing devices 150-152 and sensing circuitry 140-142 and delivered to processing circuitry 110. Sensing devices 150-152 and sensing circuitry 140-142 can deliver the signals directly to processing circuitry 110 or sensing circuitry 140-142 can modify the signals (e.g., through pre-processing) before delivering signals to processing circuitry 110.

Processing circuitry 110 may be configured to determine a set of correlation coefficient values for the values of the first and second physiological parameters, which may include blood pressure values, oxygen saturation values, and/or blood volume values. Processing circuitry 110 may associate each correlation coefficient value with a blood pressure value. Based on the correlation coefficient value(s) associated with a particular blood pressure value (and, in some examples, nearby blood pressure values), processing circuitry 110 may be configured to determine an autoregulation state value associated with the particular blood pressure value.

For example, processing circuitry 110 may be configured to determine an autoregulation state value representing an intact autoregulation state for a particular blood pressure value in response to determining that a mean of the correlation coefficient values associated with the particular blood pressure value is less than a threshold value, such as 0.5, 0.4, 0.3, 0.2, 0.1, 0.0, or any other threshold value. Processing circuitry 110 may be configured to determine an impaired autoregulation state value for a particular blood pressure value in response to determining that a mean of the correlation coefficient values associated with the particular blood pressure value is greater than the threshold value. Instead of using a mean, processing circuitry 110 may also use a median or another metric to determine autoregulation state values.

Processing circuitry 110 may be configured to determine an uncategorized autoregulation state value in response to determining that there are less than a threshold number of correlation coefficient values associated with the particular blood pressure value and the nearby blood pressure values (e.g., that there is insufficient data). In some examples, processing circuitry 110 may use bins with a width of one, two, three, four, five, six, seven, or any other measure of millimeters of mercury to determine an autoregulation state value for a particular blood pressure value. For example, to determine an autoregulation state value for a blood pressure value of eighty millimeters of mercury, processing circuitry 110 may be configured to use a bin width of five millimeters of mercury. Thus, processing circuitry 110 may be configured to determine the autoregulation state value at eighty millimeters of mercury based on the correlation coefficient values associated with 78, 79, 80, 81, and 82 millimeters of mercury.

As the blood pressure of the patient changes, processing circuitry 110 may be configured to continually or periodically determine autoregulation state values for the new blood pressure values of the patient. Thus, in a monitoring session in which the blood pressure of the patient has not been greater than one hundred millimeters of mercury, processing circuitry 110 may not have determined autoregulation state values for any blood pressure values greater than one hundred millimeters of mercury. Processing circuitry 110 may be configured to set or change an autoregulation state value associated with a particular blood pressure value as processing circuitry 110 gathers additional data at or near the particular blood pressure value (see, e.g., FIGS. 6A-6D).

Processing circuitry 110 may be configured to determine a plurality of autoregulation state values based on the data from the one or more signals received by processing circuitry 110 from sensing devices 140-142 and sensing circuitries 150-152. Processing circuitry 110 may be configured to store the plurality of autoregulation state values in a data structure stored in memory 120, such as in the form of an array or a vector. The plurality of autoregulation state values may be referred to herein as a "data structure," a "state array," or as a "state vector," where each autoregulation state value of the state array or vector is associated with a blood pressure value.

In some examples, the plurality of autoregulation state values may be arranged as a table with two columns: a first column for a blood pressure value and a second column for an autoregulation state value associated with the blood pressure value. For example, a first column of the array can include blood pressure values from, for example, one to one hundred and fifty millimeters of mercury. These minimum and maximum are merely examples. In some examples, the processing circuitry can set the minimum blood pressure value of the plurality of autoregulation state values to ten, twenty, or thirty millimeters of mercury or any other suitable minimum blood pressure value. The processing circuitry can set the maximum blood pressure value of the plurality of autoregulation state values at one hundred, one hundred and twenty, one hundred and forty, or two hundred millimeters of mercury or any suitable maximum blood pressure value. The blood pressure values in the first column may have increments of, e.g., one-half, one, or two millimeters of mercury or any other blood pressure increment, such that the first row may be associated with zero millimeters of mercury, the second row may be associated with one millimeter of mercury, the third row may be associated with two millimeters of mercury, and so on. FIGS. 6A-6D show a plurality of autoregulation state values associated with blood pressure values at increments of five millimeters of mercury.

A second column of the array can include autoregulation state values, where each autoregulation state value is associated with a blood pressure value. For example, the processing circuitry may determine that the lower limit of autoregulation (LLA) for a patient is equal to fifty millimeters of mercury and that the upper limit of autoregulation (ULA) for the patient is equal to one hundred and twenty millimeters of mercury. Accordingly, the processing circuitry can determine that the autoregulation state values between fifty and one hundred and twenty millimeters of mercury represent an intact autoregulation state and that the autoregulation state values that are less than fifty millimeters of mercury or greater than one hundred and twenty millimeters of mercury represent an impaired autoregulation state. The processing circuitry may be configured to determine that an autoregulation state value representing an impaired autoregulation state inside the limits of autoregulation is anomalous and/or that an autoregulation state value represents an intact autoregulation state outside the limits of autoregulation is anomalous.

At the beginning of a monitoring session, processing circuitry 110 may be configured to set all of the autoregulation state values in the second column to a value representing an uncategorized autoregulation state. Additionally or alternatively, processing circuitry may be configured to set the plurality of autoregulation state values based on historical patient data at the beginning of a monitoring session.

It is possible for anomalous autoregulation state values to occur in the state vector. For example, there may be a small region of uncategorized state values in the middle of a large region of categorized state values. Processing circuitry 110 may be configured to fill in the small region of uncategorized state values if the state values on both sides of the small, uncategorized region have matching values. "Filling in" means that processing circuitry 110 can change the uncategorized state values to categorized state values to match the surrounding categorized state values. Processing circuitry 110 may incorrectly create a small region of state values representing an impaired autoregulation state far above the LLA and below the ULA. To mitigate or correct these errors, processing circuitry 110 can implement an additional step (e.g., a post-processing step) in the autoregulation algorithm. The additional step can clean up the state vector (e.g., the plurality of autoregulation state values).

Processing circuitry 110 may be configured to determine that a first autoregulation state value is anomalous based on other autoregulation state values. For example, processing circuitry 110 can determine that the first autoregulation state value represents a first autoregulation state (e.g., an impaired state or an intact state) and that none of the autoregulation state values within a threshold number of blood pressure units of the first autoregulation state value (e.g., three, five, or ten millimeters of mercury) represents the first autoregulation state. This example can occur when processing circuitry 110 sets an autoregulation state value to an impaired state well inside the limits of autoregulation or sets an autoregulation state value to an intact state well outside the limits of autoregulation. Thus, processing circuitry 110 may be configured to determine that a first autoregulation state value is anomalous in response to determining that the first autoregulation state value is surrounded by autoregulation state values representing a different state. Processing circuitry 110 may be configured to modify the first autoregulation state value to match the surrounding autoregulation state values in response to this determination.

Processing circuitry 110 is also configured to determine an estimate of a limit of autoregulation of a patient based on the plurality of autoregulation state values and the modified first autoregulation state value. Processing circuitry 110 may be configured to determine that the lower limit of autoregulation is equal to the lowest blood pressure value associated with an intact autoregulation state. By modifying one or more anomalous autoregulation state values and using the modified autoregulation state values to determine the autoregulation status, processing circuitry 110 may determine a more accurate estimate of a limit of autoregulation and consequently a more accurate estimate of the autoregulation status of the patient.

Processing circuitry 110 is configured to determine an autoregulation status of the patient based on the estimate of the limit of autoregulation. For example, processing circuitry 110 may determine whether the current blood pressure value of the patient is greater than the estimate of the lower limit of autoregulation. If the current blood pressure value is greater than the estimate of the lower limit of autoregulation, then processing circuitry 110 can determine that the patient has intact autoregulation, unless the current blood pressure value is greater than the upper limit of autoregulation of the patient.

Processing circuitry 110 may be configured to output, e.g., for display via display 132 of user interface 130, an indication of the autoregulation status. To present an indication of autoregulation status, display 132 may present a graphical user interface such as graphical user interface 300, 400, or 500 shown in FIGS. 3-5. As described in further detail below, graphical user interface 300 includes an indicator of autoregulation status 350. Graphical user interfaces 400 and 500 include colors and shading as indicators of the autoregulation state values across a range of blood pressure values. The indications of autoregulation status and autoregulation state values may include text, colors, and/or audio presented to a user. Processing circuitry 110 may be further configured to present an indication of one or more limits of autoregulation (e.g., indicators 360 and 370).

By determining that a first autoregulation state value is anomalous and by modifying the first autoregulation state value, processing circuitry 110 may be configured to clean or smooth anomalies out of the set of autoregulation state values. Modifying anomalous autoregulation state values may result in a more accurate and more stable set of autoregulation state values. Regional oximetry device 100 is capable not only of modifying or updating the autoregulation state values that are associated with the current blood pressure value or nearby blood pressure values, but can also modify autoregulation state values that are far away from the current blood pressure value (e.g., at least five or ten millimeters of mercury difference). For example, regional oximetry device 100 may be configured to modify an autoregulation state value in response to determining that the autoregulation state value is anomalous, even if the autoregulation state value is more than five, ten, or twenty millimeters of mercury away from the current blood pressure value. Regional oximetry device 100 may also be configured to modify the autoregulation state value even without any new data for nearby blood pressure values, where nearby blood pressure values are within two, three, five, or ten millimeters of mercury of the current blood pressure value.

In some examples, processing circuitry 110 is configured to store the unmodified autoregulation state values to memory 120 and to determine new autoregulation state values at a later time based on the unmodified autoregulation state values. Storing the unmodified autoregulation state values may reduce the likelihood that the modification of an anomalous autoregulation state value will result in a cascade or domino effect that causes processing circuitry 110 to determine that nearby autoregulation state values are anomalous.

Although other example devices, systems, and techniques are possible, regional oximetry device 100 may be configured to determine the autoregulation state values based on COx values derived from MAP values and $rSO_2$ values. Alternatively, processing circuitry 110 may determine the autoregulation state values based on HVx values, BVS values, and/or $rSO_2$ values. Regional oximetry device 200 of FIG. 2 includes additional detail on how processing circuitry 110 can determine $rSO_2$ values based on a physiological signal received from sensing device 150.

Figure 2:
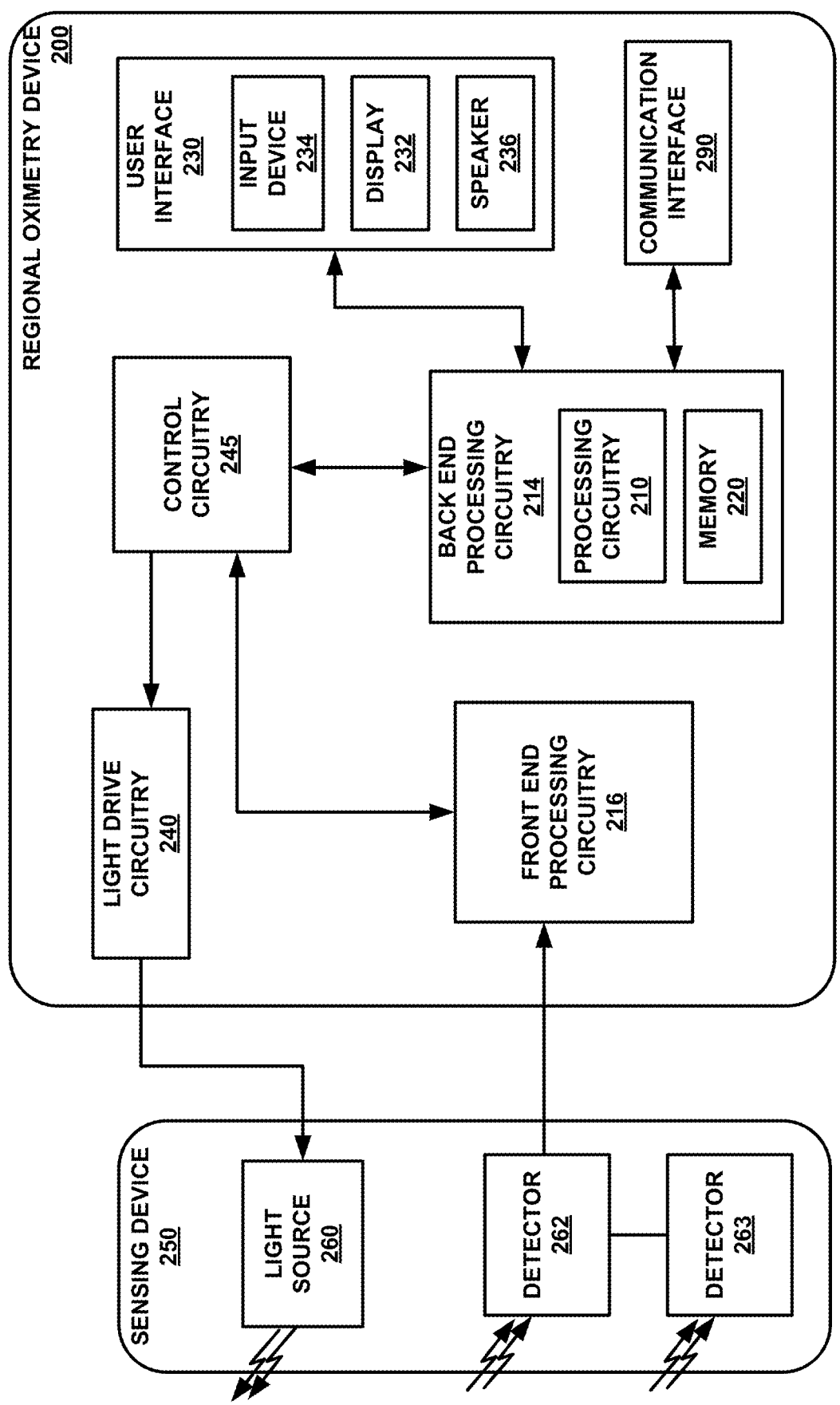
FIG. 2 is a conceptual block diagram illustrating an example regional oximetry device for monitoring the autoregulation status of a patient.

FIG. 2 is a conceptual block diagram illustrating an example regional oximetry device 200 for monitoring the autoregulation status of a patient. In the example shown in FIG. 2, regional oximetry device 200 is coupled to sensing device 250 and may be collectively referred to as a regional oximetry system, which each generate and process physiological signals of a subject. In some examples, sensing device 250 and regional oximetry device 200 may be part of an oximeter. As shown in FIG. 2, regional oximetry device 200 includes back-end processing circuitry 214, user interface 230, light drive circuitry 240, front-end processing circuitry 216, control circuitry 245, and communication interface 290. Regional oximetry device 200 may be communicatively coupled to sensing device 250. Regional oximetry device 200 is an example of regional oximetry device 100 shown in FIG. 1. In some examples, regional oximetry device 200 may also include a blood pressure sensor and/or a blood volume sensor (e.g., sensing devices 151 and 152 shown in FIG. 1).

In the example shown in FIG. 2, sensing device 250 includes light source 260, detector 262, and detector 263. In some examples, sensing device 250 may include more than two detectors. Light source 260 may be configured to emit photonic signals having two or more wavelengths of light (e.g., red and infrared (IR)) into a subject's tissue. For example, light source 260 may include a red light emitting light source and an IR light emitting light source, (e.g., red and IR light emitting diodes (LEDs)), for emitting light into the tissue of a subject to generate physiological signals. In some examples, the red wavelength may be between about 600 nm and about 700 nm, and the IR wavelength may be between about 800 nm and about 1000 nm. Other wavelengths of light may be used in other examples. Light source 260 may include any number of light sources with any suitable characteristics. In examples in which an array of sensors is used in place of sensing device 250, each sensing device may be configured to emit a single wavelength. For example, a first sensing device may emit only a red light while a second sensing device may emit only an IR light. In some examples, light source 260 may be configured to emit two or more wavelengths of near-infrared light (e.g., wavelengths between 600 nm and 1000 nm) into a subject's tissue. In some examples, light source 260 may be configured to emit four wavelengths of light (e.g., 724 nm, 770 nm, 810 nm, and 850 nm) into a subject's tissue. In some examples, the subject may be a medical patient.

As used herein, the term "light" may refer to energy produced by radiative sources and may include one or more of ultrasound, radio, microwave, millimeter wave, infrared, visible, ultraviolet, gamma ray or X-ray electromagnetic radiation. Light may also include any wavelength within the radio, microwave, infrared, visible, ultraviolet, or X-ray spectra, and that any suitable wavelength of electromagnetic radiation may be appropriate for use with the present techniques. Detectors 262 and 263 may be chosen to be specifically sensitive to the chosen targeted energy spectrum of light source 260.

In some examples, detectors 262 and 263 may be configured to detect the intensity of multiple wavelengths of near-infrared light. In some examples, detectors 262 and 263 may be configured to detect the intensity of light at the red and IR wavelengths. In some examples, an array of detectors may be used and each detector in the array may be configured to detect an intensity of a single wavelength. In operation, light may enter detector 262 after passing through the subject's tissue, including skin, bone, and other shallow tissue (e.g., non-cerebral tissue and shallow cerebral tissue). Light may enter detector 263 after passing through the subject's tissue, including skin, bone, other shallow tissue (e.g., non-cerebral tissue and shallow cerebral tissue), and deep tissue (e.g., deep cerebral tissue). Detectors 262 and 263 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detectors 262 and 263.

After converting the received light to an electrical signal, detectors 262 and 263 may send the detection signals to regional oximetry device 200, where the detection signals may be processed and physiological parameters may be determined (e.g., based on the absorption of the red and IR wavelengths in the subject's tissue at both detectors). In some examples, one or more of the detection signals may be preprocessed by sensing device 250 before being transmitted to regional oximetry device 200. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation," the entire content of which is incorporated herein by reference.

Control circuitry 245 may be coupled to light drive circuitry 240, front-end processing circuitry 216, and back-end processing circuitry 214, and may be configured to control the operation of these components. In some examples, control circuitry 245 may be configured to provide timing control signals to coordinate their operation. For example, light drive circuitry 240 may generate one or more light drive signals, which may be used to turn on and off light source 260, based on the timing control signals provided by control circuitry 245. Front-end processing circuitry 216 may use the timing control signals to operate synchronously with light drive circuitry 240. For example, front-end processing circuitry 216 may synchronize the operation of an analog-to-digital converter and a demultiplexer with the light drive signal based on the timing control signals. In addition, the back-end processing circuitry 214 may use the timing control signals to coordinate its operation with front-end processing circuitry 216.

Light drive circuitry 240, as discussed above, may be configured to generate a light drive signal that is provided to light source 260 of sensing device 250. The light drive signal may, for example, control the intensity of light source 260 and the timing of when light source 260 is turned on and off. In some examples, light drive circuitry 240 provides one or more light drive signals to light source 260. Where light source 260 is configured to emit two or more wavelengths of light, the light drive signal may be configured to control the operation of each wavelength of light. The light drive signal may include a single signal or may comprise multiple signals (e.g., one signal for each wavelength of light).

Front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. Front-end processing circuitry 216 may operate on the analog or digital form of the detector signals to separate out different components of the signals. Front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. Front-end processing circuitry 216 may decrease the number of samples in the digital detector signals. In some examples, front-end processing circuitry 216 may also remove dark or ambient contributions to the received signal.

Back-end processing circuitry 214 may include processing circuitry 210 and memory 220. Processing circuitry 210 may include an assembly of analog or digital electronic components and may be configured to execute software, which may include an operating system and one or more applications, as part of performing the functions described herein with respect to, e.g., processing circuitry 110. Processing circuitry 210 may receive and further process one or more signals received from front-end processing circuitry 216. For example, processing circuitry 210 may determine physiological parameter values based on the received signals. For example, processing circuitry 210 may compute one or more of regional oxygen saturation, blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof.

Processing circuitry 210 may perform any suitable signal processing of a signal, such as any suitable band-pass filtering, adaptive filtering, closed-loop filtering, any other suitable filtering, and/or any combination thereof. Processing circuitry 210 may also receive input signals from additional sources not shown. For example, processing circuitry 210 may receive an input signal containing information about treatments provided to the subject from user interface 230. Additional input signals may be used by processing circuitry 210 in any of the determinations or operations it performs in accordance with back-end processing circuitry 214 or regional oximetry device 200.

Processing circuitry 210 is an example of processing circuitry 110 and is configured to perform the techniques of this disclosure. For example, processing circuitry 210 is configured to receive signals indicative of physiological parameters including a blood pressure of the patient. Processing circuitry 210 is also configured to determine autoregulation state values based on the received signals and determine that one of the autoregulation state values is anomalous. Processing circuitry 210 may be configured to modify the anomalous autoregulation state value based on other autoregulation state value. Processing circuitry 210 is also configured to determine an autoregulation status of the patient based on the autoregulation state values including the modified autoregulation state value.

Memory 220 may include any suitable computer-readable media capable of storing information that can be interpreted by processing circuitry 210. In some examples, memory 220 may store autoregulation state values including modified and unmodified values, correlation coefficient values, threshold rates, threshold values, smoothing functions, Gaussian filters, confidence metrics, expected autoregulation functions, historical patient data, physiological parameter values, such as blood oxygen saturation, pulse rate, blood pressure, or any combination thereof, in a memory device for later retrieval. Back-end processing circuitry 214 may be communicatively coupled with user interface 230 and communication interface 290.

User interface 230 may include input device 234, display 232, and speaker 236. User interface 230 is an example of user interface 130 shown in FIG. 1, and display 232 is an example of display 132 shown in FIG. 1. User interface 230 may include, for example, any suitable device such as one or more medical devices (e.g., a medical monitor that displays various physiological parameters, a medical alarm, or any other suitable medical device that either displays physiological parameters or uses the output of back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

Input device 234 may include any type of user input device such as a keyboard, a mouse, a touch screen, buttons, switches, a microphone, a joystick, a touch pad, or any other suitable input device or combination of input devices. In other examples, input device 234 may be a pressure-sensitive or presence-sensitive display that is included as part of display 232. Input device 234 may also receive inputs to select a model number of sensing device 250, blood pressure sensor 250 (FIG. 2), or blood pressure processing equipment. In some examples, processing circuitry 210 may determine a threshold rate and/or a length of a window of time based on user input received from input device 234.

Figure 3:
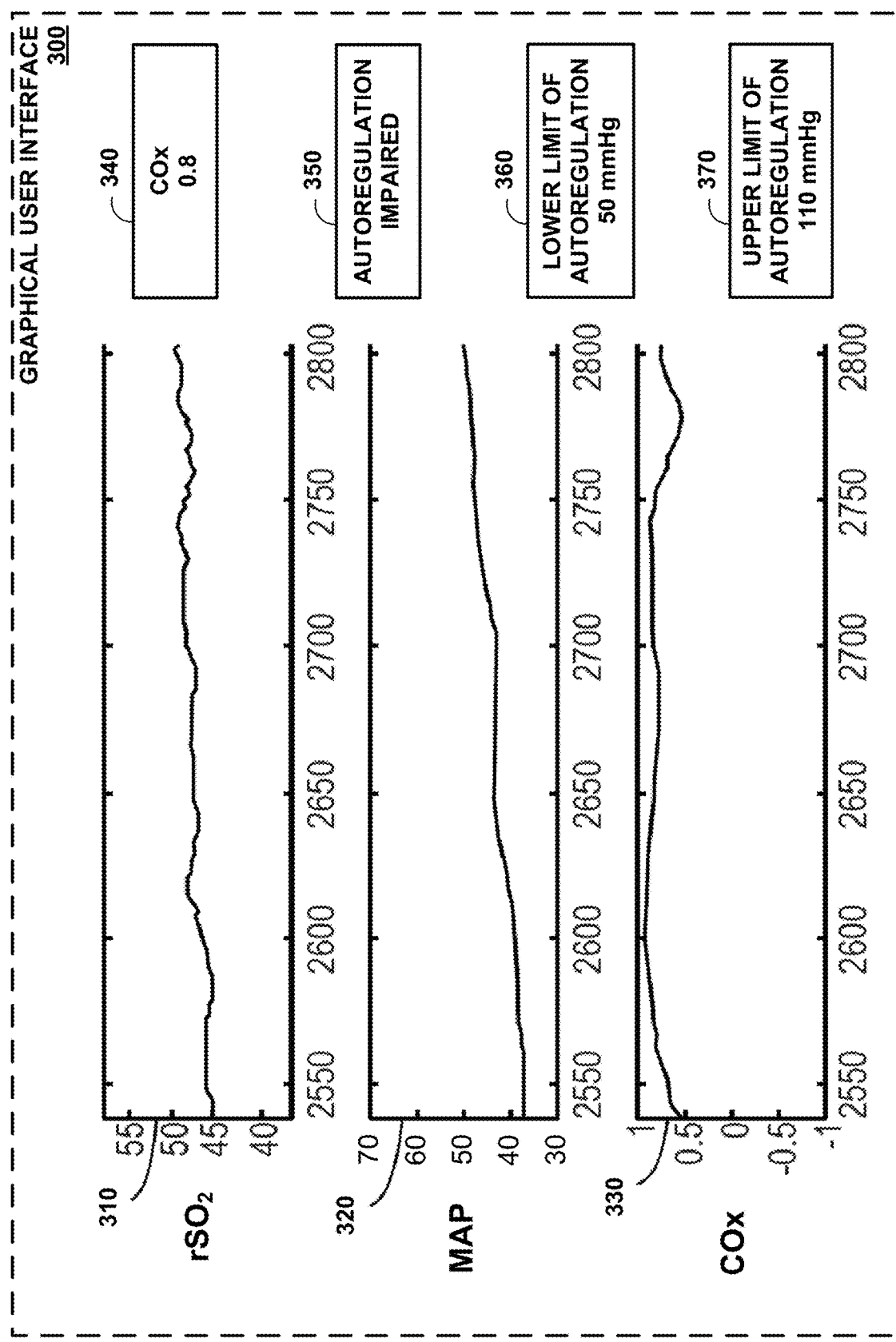
FIG. 3 illustrates an example graphical user interface including autoregulation information presented on a display.

In some examples, the subject may be a medical patient and display 232 may exhibit a list of values which may generally apply to the subject, such as, for example, an oxygen saturation signal indicator, a blood pressure signal indicator, a COx signal indicator, a COx value indicator, and/or an autoregulation status indicator. Display 232 may also be configured to present additional physiological parameter information. Graphical user interface 300 shown in FIG. 3 is an example of an interface that can be presented via display 232 of FIG. 2. Additionally, display 232 may present, for example, one or more estimates of a subject's regional oxygen saturation generated by regional oximetry device 200 (referred to as an "$rSO_2$" measurement). Display 232 may also present indications of the upper and lower limits of autoregulation. Speaker 236 within user interface 230 may provide an audible sound that may be used in various examples, such as for example, sounding an audible alarm in the event that the autoregulation status of a patient is impaired or that the patient's physiological parameters are not within a predefined normal range.

Communication interface 290 may enable regional oximetry device 200 to exchange information with external devices. Communication interface 290 may include any suitable hardware, software, or both, which may allow regional oximetry device 200 to communicate with electronic circuitry, a device, a network, a server or other workstations, a display, or any combination thereof. For example, regional oximetry device 200 may receive MAP values and/or oxygen saturation values from an external device via communication interface 290.

The components of regional oximetry device 200 that are shown and described as separate components are shown and described as such for illustrative purposes only. In some examples the functionality of some of the components may be combined in a single component. For example, the functionality of front-end processing circuitry 216 and back-end processing circuitry 214 may be combined in a single processor system. Additionally, in some examples the functionality of some of the components of regional oximetry device 200 shown and described herein may be divided over multiple components. For example, some or all of the functionality of control circuitry 245 may be performed in front-end processing circuitry 216, in back-end processing circuitry 214, or both. In other examples, the functionality of one or more of the components may be performed in a different order or may not be required. In some examples, all of the components of regional oximetry device 200 can be realized in processor circuitry.

FIG. 3 illustrates an example graphical user interface 300 including autoregulation information presented on a display. FIG. 3 is an example of a presentation by processing circuitry 110 on display 132 shown in FIG. 1 or by processing circuitry 210 on display 232 shown in FIG. 2. Graphical user interface 300 may be configured to display various information related to blood pressure, oxygen saturation, the COx index, limits of autoregulation, and/or autoregulation status. As shown, graphical user interface 300 may include oxygen saturation signal indicator 310, blood pressure signal indicator 320, and COx signal indicator 330. Graphical user interface 300 may include COx value indicator 340, autoregulation status indicator 350, and limit of autoregulation indicators 360 and 370.

Blood pressure signal indicator 320 may present a set of MAP values determined by processing circuitry 110 of regional oximetry device 100. In some examples, blood pressure signal indicator 320 may present MAP values as discrete points over time or in a table. Blood pressure signal indicator 320 may also present MAP values as a moving average or waveform of discrete points. Blood pressure signal indicator 320 may present MAP values as a single value (e.g., a number) representing a current MAP value. Oxygen saturation signal indicator 310 and COx signal indicator 330 may also present rSO2 values and COx values, respectively, as discrete points, in a table, as a moving average, as a waveform, and/or as a single value.

COx signal indicator 330 may present a set of correlation coefficient values determined by processing circuitry 110. Processing circuitry 110 may determine the correlation coefficient values as a function of the oxygen saturation values presented in oxygen saturation signal indicator 310 and the MAP values presented in blood pressure signal indicator 320. In some examples, a COx value at or near one indicates the autoregulation status of a patient is impaired, as shown in autoregulation status indicator 350.

Processing circuitry 110 may determine a set of correlation coefficient values and associated blood pressure values using the values presented in indicators 310, 320, and/or 330. Processing circuitry 110 may determine autoregulation state values based on the correlation coefficient values associated with a range of blood pressure values. As the blood pressure of the patient changes, processing circuitry 110 can determine new correlation coefficient values at the most recent blood pressure value. Processing circuitry 110 can also determine an autoregulation state value for the most recent blood pressure value. Thus, processing circuitry 110 may be configured to update (or leave unchanged) the autoregulation state value at the most recent blood pressure value.

Processing circuitry 110 may be configured to determine an estimate of a limit of autoregulation based on the autoregulation state values across a range of blood pressure values. For example, processing circuitry 110 may determine a lower limit of autoregulation at forty millimeters of mercury based on the nearby correlation coefficient values (e.g., the correlation coefficient values from thirty to fifty millimeters of mercury). Thus, processing circuitry 110 may be configured to change or set autoregulation state values at or near the most recent blood pressure value.

However, according to the techniques of this disclosure, processing circuitry 110 may also be configured to identify and modify anomalous autoregulation state values, even if the anomalous autoregulation state values are separated from the current blood pressure value by more than five or ten millimeters of mercury. For example, processing circuitry 110 can identify an autoregulation state value as anomalous if the autoregulation state value represents a first autoregulation state and most or all of the nearby autoregulation state values represent another autoregulation state.

COx value indicator 340 shows a COx value of 0.8, which may result in a determination by processing circuitry 110 that the autoregulation status of the patient is impaired. Processing circuitry 110 may be configured to present, as the COx value in COx value indicator 340, the most recently determined COx value or a moving average of recently determined COx values. To determine the autoregulation status of a patient for presentation in autoregulation status indicator 350, processing circuitry 110 may determine whether the most recent MAP value shown in blood pressure signal indicator 320 is between the limits of autoregulation presented in limit of autoregulation indicators 360 and 370. In examples in which processing circuitry 110 determines that the current autoregulation status is impaired, processing circuitry 110 may be configured to set the autoregulation state value associated with the current blood pressure value of the patient to a value representing an impaired autoregulation state.

Processing circuitry 110 may present limit of autoregulation indicators 360 and/or 370 in terms of blood pressure, for example, in units of millimeters of mercury (mmHg). Processing circuitry 110 can determine the limits of cerebral autoregulation (LLA and ULA) for presentation in indicators 360 and 370 based on a relationship between the blood pressure of a patient and another physiological parameter of the patient. For example, processing circuitry 110 can highlight indicator 350 and/or indicator 360 when the most recent blood pressure of the patient is outside of the LLA, or processing circuitry 110 can highlight indicator 350 and/or 370 when the most recent blood pressure of the patient is outside of the ULA. In other examples, a single indicator may present the type of limit that has been exceed by the MAP value. If the LLA or ULA change, processing circuitry 110 may control user interface 300 to change the value of the LLA or ULA in accordance with any change to that respective value.

Processing circuitry 110 may determine an estimate of a lower limit of autoregulation presented in indicator 360 and/or an estimate of an upper limit of autoregulation presented in indicator 370. Processing circuitry 110 may determine the estimates based on a set of correlation coefficient values including one or more updated values. Processing circuitry 110 may be configured to generate a notification in response to determining that the MAP value is less than or equal to the estimate of the lower limit of autoregulation. Processing circuitry 110 may output the notification in autoregulation status indicator 350 as text, color, blinking, and/or any other suitable visible or audible manner.

In some examples, processing circuitry 110 may be configured to determine that an autoregulation state value outside of the limits of autoregulation represents an intact autoregulation state. In the example of FIG. 3, blood pressure values less than fifty millimeters of mercury and greater than one hundred and ten millimeters of mercury are outside of the limits of autoregulation. Processing circuitry 110 may determine an autoregulation state value representing an intact autoregulation state at a blood pressure value outside of the limits of autoregulation, such as at thirty millimeters of mercury. Processing circuitry 110 may be configured to identify the autoregulation state value associated with thirty millimeters of mercury as anomalous because the lower limit of autoregulation is greater than thirty millimeters of mercury, and yet the autoregulation state value has been designated as representing an intact autoregulation state. Responsive to determining that the autoregulation state value associated with thirty millimeters of mercury is anomalous, processing circuitry 110 may be configured to set the autoregulation state value associated with thirty millimeters of mercury to an autoregulation state value representing an impaired autoregulation state.

Similarly, processing circuitry 110 may determine an autoregulation state value representing an impaired autoregulation state at a blood pressure value inside of the limits of autoregulation, which is between fifty and one hundred and ten millimeters of mercury in the example of FIG. 3. Processing circuitry 110 may be configured to identify an autoregulation state value associated with seventy millimeters of mercury as anomalous because the lower limit of autoregulation is less than seventy millimetres of mercury, the upper limit of autoregulation is greater than seventy millimetres of mercury, and yet has been designated as representing an impaired autoregulation state. Responsive to determining that the autoregulation state value associated with seventy millimeters of mercury is anomalous, processing circuitry 110 may be configured to set the autoregulation state value associated with seventy millimeters of mercury to an autoregulation state value representing an intact autoregulation state.

Figure 4:
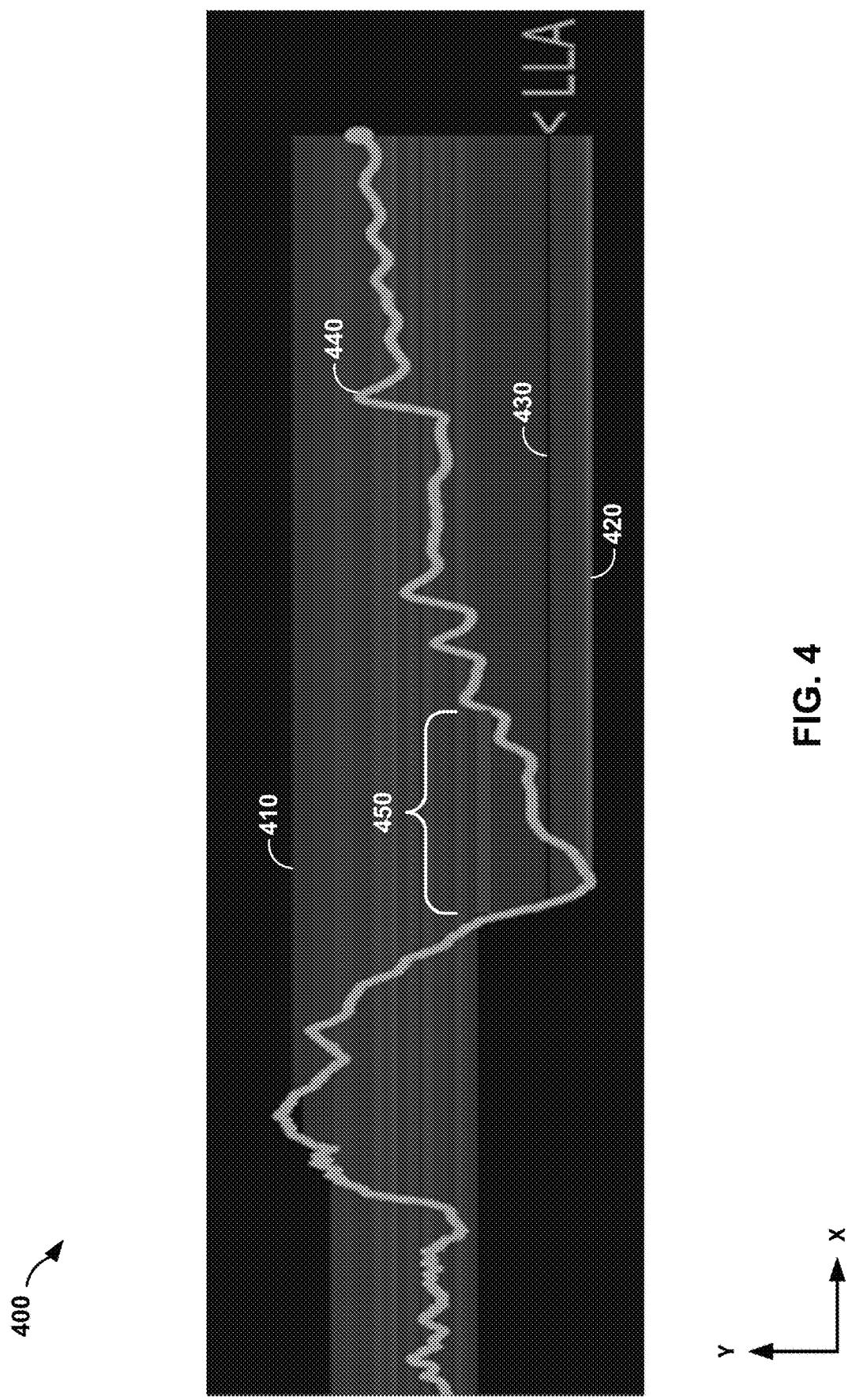
FIGS. 4 and 5 depict graphs illustrating blood pressure over time, a plurality of autoregulation state values, and the lower limit of autoregulation, in accordance with some examples of this disclosure.
Figure 5:
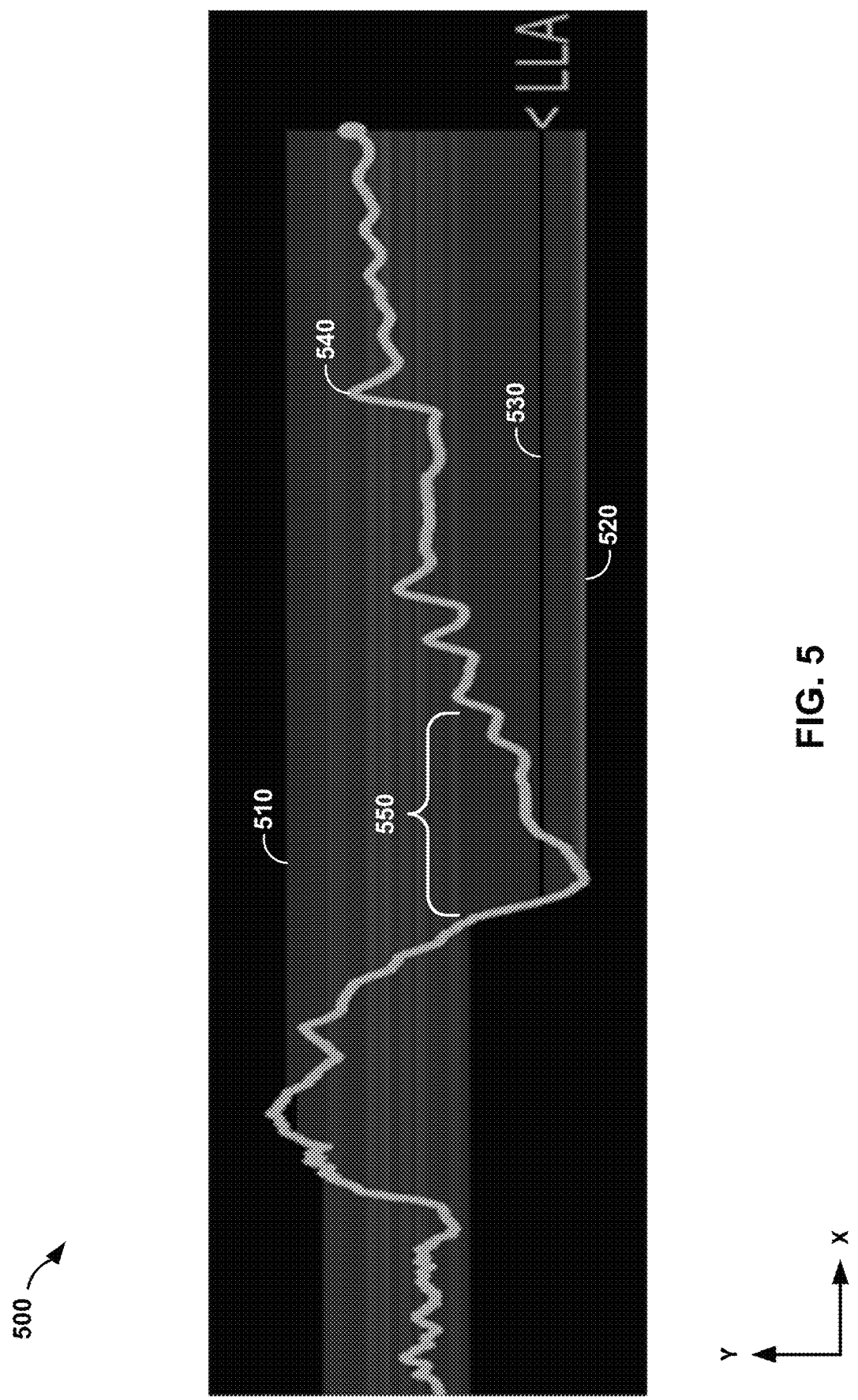

FIGS. 4 and 5 depict graphs 400 and 500 illustrating blood pressure over time, a plurality of autoregulation state values, and the lower limit of autoregulation, in accordance with some examples of this disclosure. Processing circuitry 110 or 214 may be configured to present graph 400 and/or 500 via display 132 or 232 or on graphical user interface 300. Processing circuitry 110 can present graphs 400 and 500 to show indications 440 and 540 of blood pressure values of a patient over time.

Processing circuitry 110 can also present an indication of cerebral autoregulation status in graphs 400 and 500 by, for example, presenting indications 440 and 540 between or outside of LLA 430 and the upper limit of autoregulation (not shown in FIGS. 4 and 5). Time is represented along the x-axis of graphs 400 and 500, and blood pressure is represented along the y-axis of graphs 400 and 500. The state vector or plurality of autoregulation state values at any time represents and can be considered as a slice or cross-section of graphs 400 and 500 in the y-axis direction.

The region above LLAs 430 and 530 and below the ULAs (not shown in FIGS. 4 and 5) is the safe (e.g., intact) zone or region. The region below LLAs 430 and 530 is the unsafe (e.g., impaired) zone. Processing circuitry 110 may be configured to present graph 400 and/or 500 via display 132 with colors to indicate the plurality of autoregulation state values. For example, processing circuitry 110 can present a green color for autoregulation state values representing an intact autoregulation state, a red color for autoregulation state values representing an impaired autoregulation state, and a black color for autoregulation state values representing an uncategorized autoregulation state. Processing circuitry 110 may be configured to output, for display, data indicative of a color for a modified autoregulation state value responsive to determining that modified autoregulation state value represents a respective autoregulation state. FIGS. 4 and 5 depicts these colors in greyscale as different shades of grey.

Processing circuitry 110 may be configured to determine the blood pressure value associated with LLA 430 when the blood pressure of the patient (shown by indicator 440) crosses the blood pressure value associated with LLA 430. In the examples of FIGS. 4 and 5, processing circuitry 110 does not determine the upper limit of autoregulation because the blood pressure of the patient does not cross the blood pressure value associated with the upper limit of autoregulation. In the examples of FIGS. 4 and 5, blood pressure values 410 and 510 are the highest blood pressure values associated with a categorized autoregulation state value. Blood pressure values 420 and 520 are the lowest blood pressure values associated with a categorized autoregulation state value. The blood pressure values greater than blood pressure value 410 and 510 and the blood pressure values less than blood pressure values 420 and 520 are associated with uncategorized values because processing circuitry 110 has insufficient data to set the autoregulation state values in these regions.

FIG. 4 depicts one or more anomalous autoregulation state values in time period 450. At the beginning of the time period 450, indicator 440 crosses the blood pressure values associated with the anomalous autoregulation state values. In the example of FIG. 4, processing circuitry 110 has determined that the anomalous autoregulation state values represent an impaired autoregulation state even though the associated blood pressure values are inside the limits of autoregulation. The anomalous region of state values representing an impaired autoregulation state is small, isolated, and surrounded by state values representing an intact autoregulation state.

At the end of time period 450, indicator 440 crosses the blood pressure values associated with the anomalous autoregulation state values, and processing circuitry 110 sets the anomalous autoregulation state values to a value representing an intact autoregulation state. In the example of FIG. 4, processing circuitry 110 can set or change the anomalous autoregulation state values based on new data when the blood pressure of the patient crosses through the blood pressure values associated with the anomalous autoregulation state values.

In accordance with the techniques of this disclosure, processing circuitry 110 may be configured to identify and modify the anomalous autoregulation state values before the blood pressure of the patient crosses through the blood pressure values associated with the anomalous autoregulation state values. Processing circuitry 110 may be configured to identify a set of autoregulation state values representing an intact autoregulation state. In the example of FIG. 4, the set of intact autoregulation state values may be associated with blood pressure values from LLA 430 to blood pressure value 410. Processing circuitry 110 may then determine that the anomalous autoregulation state values are inside of the set of intact autoregulation state values.

In some examples, processing circuitry 110 may also be configured to determine a set of impaired autoregulation state values at blood pressure values less than LLA 430. Processing circuitry 110 may then be configured to determine that the difference between the blood pressure values associated with anomalous autoregulation state values and the blood pressure values associated with the set of impaired autoregulation state values is greater than a threshold value, such as ten, fifteen, or twenty millimeters of mercury. Graph 500 shows that processing circuitry 110 has modified the anomalous autoregulation state values to have a state value representing an intact autoregulation state value in response to determining that the anomalous autoregulation state values are far away in terms of blood pressure from the set of impaired autoregulation state values below LLA 430 (e.g., greater than a threshold amount away from the set of impaired autoregulation state values).

In some examples, processing circuitry 110 may be configured to modify an anomalous autoregulation state value that represents an intact or impaired autoregulation state (e.g., a categorized value) to an uncategorized value to indicate that processing circuitry 110 is not sure of the correct state. Alternatively, processing circuitry 110 may be configured to replace the anomalous categorized state values with the opposite categorized state values (e.g., replace an anomalous impaired state value with an intact state value).

Processing circuitry 110 may be configured to determine whether to set the anomalous autoregulation state value to a categorized or uncategorized state value based on a confidence of the surrounding state or some other confidence metric. For example, processing circuitry 110 may be configured to determine a confidence metric for autoregulation state values associated with blood pressure values within a threshold value from the first blood pressure value. Processing circuitry 110 may be configured to set the anomalous autoregulation state value to an uncategorized autoregulation value in response to determining that the confidence metric is less than the threshold confidence level.

As stated above, processing circuitry 110 may be configured to determine a confidence metric for the autoregulation state values associated with blood pressure values within a threshold value from the blood pressure value associated with the first autoregulation state value. The confidence metric may indicate whether the surrounding autoregulation state values are consistent, which may support processing circuitry 110 setting the first autoregulation state value to the predominant autoregulation state value of the surrounding autoregulation state values.

Processing circuitry 110 can determine whether the confidence metric is greater than a threshold confidence level. For example, if six of the ten surrounding autoregulation state values have an autoregulation state value representing a particular autoregulation state, the particular autoregulation state may be the predominant state, but the confidence metric may be less than a threshold confidence level. If nine of the ten surrounding autoregulation state values have an autoregulation state value representing the predominant particular autoregulation state, processing circuitry 110 may determine that the confidence metric is greater than a threshold confidence level. Processing circuitry 110 may then set the first autoregulation state value to the predominant autoregulation value in response to determining that the confidence metric is greater than the threshold confidence level.

FIGS. 6A-6D are block diagrams illustrating example data structures 602A-602D storing a plurality of autoregulation state values that are updated by processing circuitry of a regional oximetry device. In the example of FIG. 6A, processing circuitry 110 determines blood pressure value 600A of the patient to be fifty millimeters of mercury. Processing circuitry 110 also determines the lower limit of autoregulation to be associated with blood pressure values between fifty and fifty-five millimeters of mercury.

FIG. 6A depicts data structure 602A, which may also be referred to as "a state vector," including eight blood pressure values and eight autoregulation state values. The blood pressure values are spaced at intervals of five millimeters of mercury, but other spacings, including one, two, or three millimeters of mercury, are possible. In some examples, processing circuitry 110 determines data structure 602A having one hundred and fifty autoregulation state values associated with blood pressure values ranging from one to one hundred and fifty millimeters of mercury. Thus, data structures 602A-602D may be simplified versions of a state vector across thirty millimeters of mercury with a resolution of five millimeters of mercury.

In the example of data structure 602B shown in FIG. 6B, processing circuitry 110 determines blood pressure value 600B of the patient to be fifty-five millimeters of mercury. Based on data collected at the latest blood pressure value, processing circuitry 110 sets the autoregulation state value associated with fifty-five millimeters of mercury to a state value representing an impaired autoregulation state. Processing circuitry 110 can determine a state value representing an impaired autoregulation state based on determining that a mean or median of the correlation coefficients associated with fifty-five millimeters of mercury are greater than a threshold such as 0.3 or 0.5. Processing circuitry 110 also determines the lower limit of autoregulation to be associated with blood pressure values between fifty-five and sixty millimeters of mercury.

In the example of data structure 602C shown in FIG. 6C, processing circuitry 110 determines blood pressure value 600C of the patient to be sixty millimeters of mercury. Based on data collected at the most recent blood pressure value, processing circuitry 110 sets (e.g., maintains) the autoregulation state value associated with sixty millimeters of mercury at a state value representing an intact autoregulation state. Processing circuitry 110 can maintain the state value representing an intact autoregulation state based on determining that a mean or median of the correlation coefficients associated with sixty millimeters of mercury are less than a threshold such as 0.3 or 0.5. From FIG. 6B to FIGS. 6C and 6D, processing circuitry 110 does not change the lower limit of autoregulation, which is associated with blood pressure values between fifty-five and sixty millimeters of mercury.

In the example of FIG. 6D, processing circuitry 110 determines blood pressure value 600D of the patient to be sixty-five millimeters of mercury. Based on data collected at the most recent blood pressure value, processing circuitry 110 sets the autoregulation state value associated with sixty-five millimeters of mercury to a state value representing an intact autoregulation state. The autoregulation state value associated with sixty-five millimeters of mercury was previously set to an uncategorized state (see FIGS. 6A-6C). In the example of FIG. 6D, processing circuitry 110 may now have sufficient data to categorize the state value associated with sixty-five millimeters of mercury.

In the example of data structure 602D shown in FIG. 6D, processing circuitry 110 may be configured to identify the autoregulation state value associated with seventy millimeters of mercury, which represents an uncategorized autoregulation state, as anomalous. Processing circuitry 110 can determine that an uncategorized autoregulation state value is anomalous based on determining that a first set of autoregulation state values associated with blood pressure values higher than seventy millimeters of mercury has a categorized state. In the example of FIG. 6D, the autoregulation state value at seventy-five millimeters of mercury has a categorized value representing an intact autoregulation state. Processing circuitry 110 can also determine that a second set of autoregulation state values associated with blood pressure values lower than seventy millimeters of mercury has the same categorized state. In the example of FIG. 6D, the autoregulation state values at sixty and sixty-five millimeters of mercury have a categorized value representing an intact autoregulation state.

Responsive to determining that a first autoregulation state value is surrounded by a different type or category of state value, processing circuitry 110 can modify the first autoregulation state value to match the surrounding type or category of value. For example, based on determining that an uncategorized autoregulation state value at seventy millimeters of mercury is surrounded by categorized, intact autoregulation state values at sixty, sixty-five, and seventy-five millimeters of mercury, processing circuitry 110 may be configured to modify the autoregulation state value associated with seventy millimeters of mercury to represent an intact autoregulation state. Modifying the autoregulation state value associated with seventy millimeters of mercury may remove or correct anomalous values from data structure 602D and improve the presentation of the autoregulation status of the patient and the intact region of autoregulation (see FIG. 5).

In examples in which processing circuitry 110 determines that the autoregulation state value at seventy millimeters of mercury is anomalous and modifies the autoregulation state value, processing circuitry 110 may be further configured to store the unmodified (e.g., pre-corrected) state value to memory 120. In the example of FIG. 6D, the unmodified state value associated with seventy millimeters of mercury is an uncategorized state value, and the modified state value will represent an intact autoregulation state because the nearby state values also represent an intact autoregulation state. After modifying the autoregulation state value associated with seventy millimeters of mercury, processing circuitry 110 may be configured to determine new autoregulation state values based on the unmodified value associated with seventy millimeters of mercury. Using the unmodified value may reduce the chance that an erroneous modification or correction results in a future erroneous modification or correction. Additionally or alternatively, processing circuitry 110 can use the modified values to determine whether an autoregulation state value is anomalous.

Figure 7:
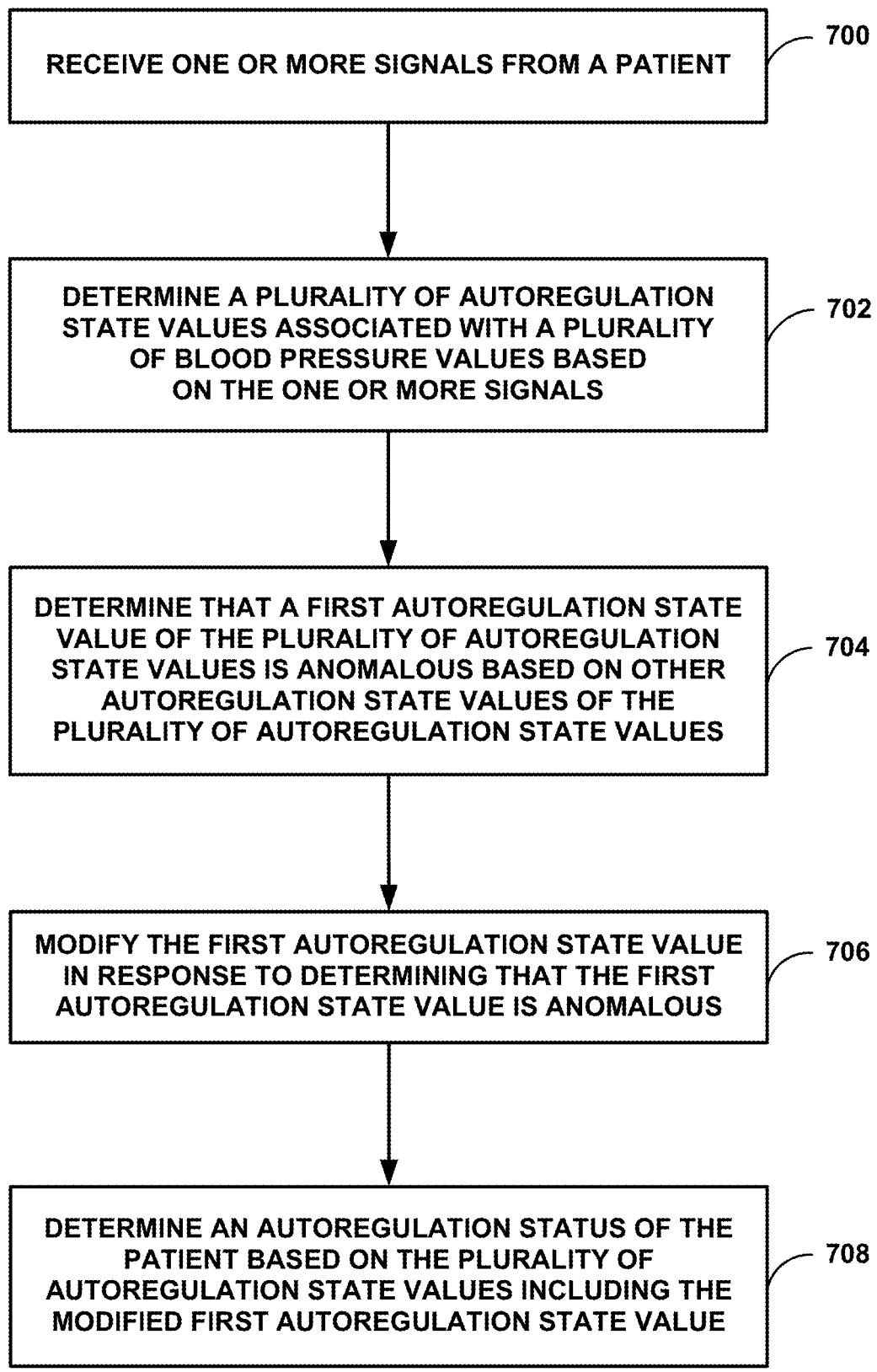
FIGS. 7 and 8 are flow diagrams illustrating example techniques for determining that an autoregulation state value is anomalous, in accordance with some examples of this disclosure.
Figure 8:
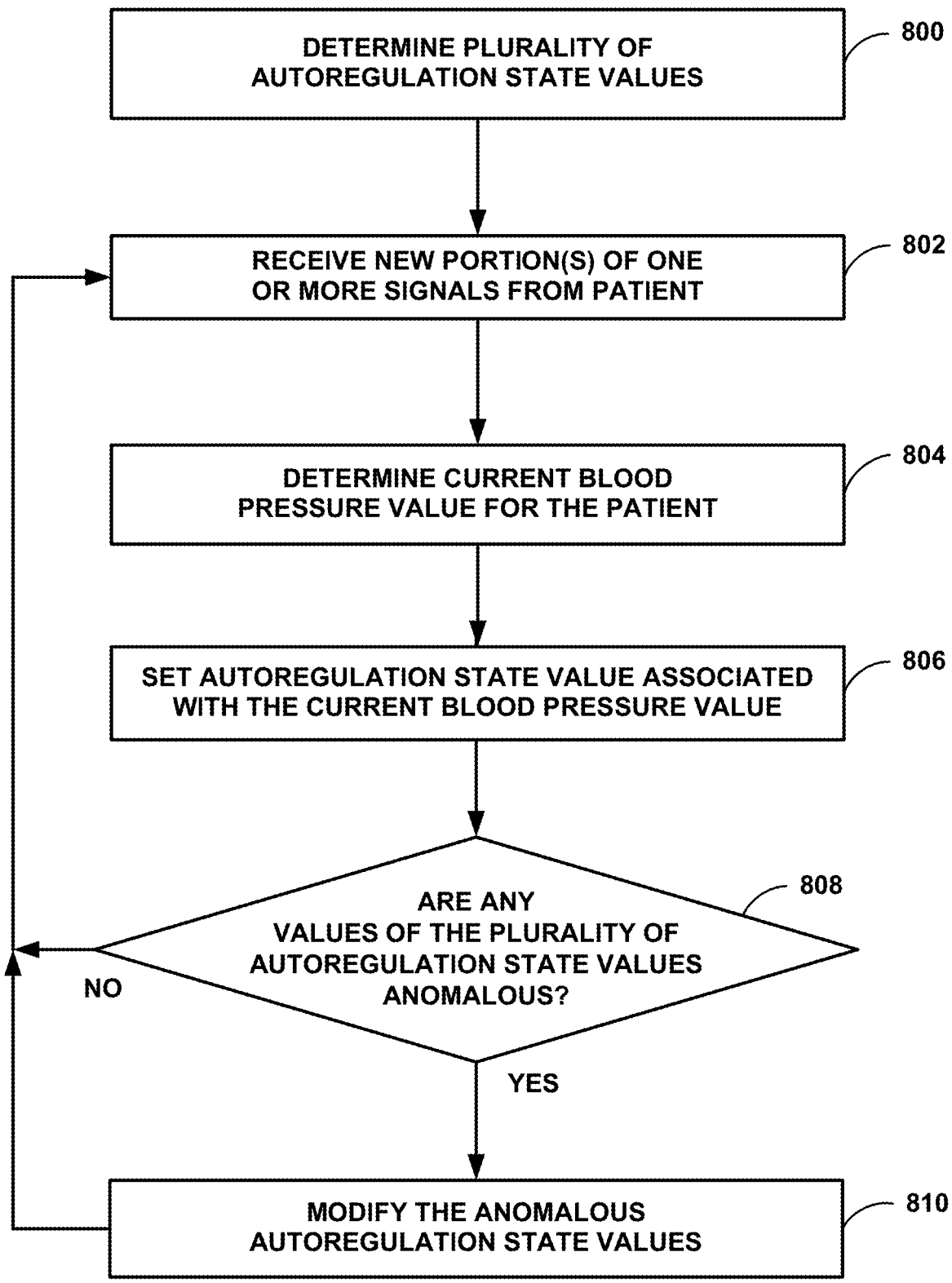

FIGS. 7 and 8 are flow diagrams illustrating example techniques for determining that an autoregulation state value is anomalous, in accordance with some examples of this disclosure. Although FIGS. 7 and 8 are described with respect to processing circuitry 110 of regional oximetry device 100 (FIG. 1), in other examples, processing circuitry 210, 214, and/or 216 (FIG. 2), alone or in combination with processing circuitry 110, may perform any part of the techniques of FIGS. 7 and 8.

In the example of FIG. 7, processing circuitry 110 receives one or more signals from a patient (700). Processing circuitry 110 can receive a signal indicating blood pressure from sensing circuitry 141, a signal indicating oxygen saturation from sensing circuitry 140, and a signal indicating blood volume from sensing circuitry 142. Processing circuitry 110 may be configured to determine blood pressure values based on the signal received from sensing circuitry 141. Processing circuitry 110 may also be configured to determine correlation coefficient values based on the blood pressure values and values of another physiological parameter.

In the example of FIG. 7, processing circuitry 110 determines a plurality of autoregulation state values associated with a plurality of blood pressure values based on the one or more signals (702). Processing circuitry 110 can determine an autoregulation state value associated with the most recent blood pressure value based at least in part on the correlation coefficient values associated with the most recent blood pressure value and nearby blood pressure values. Processing circuitry 110 can store the autoregulation state values to memory 120, such as in a data structure in the form of an array or a vector.

In the example of FIG. 7, processing circuitry 110 determines that a first autoregulation state value of the plurality of autoregulation state values is anomalous based on other autoregulation state values of the plurality of autoregulation state values (704). For example, processing circuitry can determine that an autoregulation state value is anomalous based on the nearby autoregulation state values. In examples in which a first autoregulation state value is surrounded by autoregulation state values that represent a different autoregulation state, processing circuitry 110 may be configured to identify the first autoregulation state value as anomalous.

In some examples, processing circuitry 110 can determine that a first autoregulation state value is anomalous by determining that a difference between the blood pressure value associated with the first autoregulation state value and each of a set of blood pressure values associated with a set of autoregulation state values is greater than a threshold value. In examples in which the first autoregulation state value and the set of autoregulation state values represent the same autoregulation state, the distance between the first autoregulation state value and the set of autoregulation state values may indicate whether the first autoregulation state value is anomalous or incorrect. A state value representing an intact autoregulation state that is far away from, in terms of blood pressure value, other state values representing an intact autoregulation state may be an anomalous or incorrect value.

In some examples, in examples in which the difference between the blood pressure value associated with the first autoregulation state value and the blood pressure values associated with all of the other autoregulation state values that represent the same autoregulation state, processing circuitry 110 can determine that the first autoregulation state value is anomalous. Processing circuitry 110 may determine that there are two correct sets or regions of impaired autoregulation state values (e.g., above the ULA and below the LLA) and only one set or region of impaired autoregulation state values, so the process of determining an anomalous autoregulation state value may be different for intact and impaired autoregulation state values.

Processing circuitry 110 can also identify small sets of autoregulation state values (set of two, three, or four values) that represent the same autoregulation state and are clustered together far away from all of the other autoregulation state values representing the same autoregulation state. Processing circuitry 110 may search for these small sets because two adjacent anomalous values can reinforce each other if processing circuitry 110 compares individual state values to all of the surrounding state values. In examples in which three values representing an impaired state are in a large region of state values representing an intact state, processing circuitry 110 may not determine a sufficiently high confidence metric to modify all three values because the three values may reduce the confidence in the surrounding intact values. Thus, processing circuitry 110 may be configured to identify a small cluster of autoregulation state values as anomalous in response to determining that a distance (difference in blood pressure values) from other autoregulation state values representing the same autoregulation state is greater than a threshold value.

Responsive to determining that the distance between the first autoregulation state value and the set of autoregulation state values representing the same autoregulation state as the first autoregulation state value is greater than a threshold value, processing circuitry 110 can set the first autoregulation state value to represent the autoregulation state of the autoregulation state values surrounding the first autoregulation state value (e.g., the predominant state value of the surrounding or nearby autoregulation state values). Alternatively, processing circuitry 110 can set the first autoregulation state value to an uncategorized state value in response to, for example, determining that a confidence metric for the surrounding autoregulation state values is less than a threshold value.

In the example of FIG. 7, processing circuitry 110 modifies the first autoregulation state value in response to determining that the first autoregulation state value is anomalous (706). Processing circuitry 110 can modify the first autoregulation state value by setting the first autoregulation state value to the value of nearby autoregulation state values.

In the example of FIG. 7, processing circuitry 110 determines an autoregulation status of the patient based on the plurality of autoregulation state values including the modified first autoregulation state value (708). Processing circuitry 110 can present an indication of the autoregulation status of the patient via display 132 (such as, for example, indicator of autoregulation status 350 shown in FIG. 3).

In the example of FIG. 8, processing circuitry 110 determines a plurality of autoregulation state values for a patient (800). Processing circuitry 110 can associate each autoregulation state value with a blood pressure value and store the plurality of autoregulation state values and the blood pressure values to memory 120. Processing circuitry 110 can determine each autoregulation state value based on signals received via sensing circuitry 140-142 indicating physiological parameters of a patient.

In the example of FIG. 8, processing circuitry 110 receives new portion(s) of one or more signals from the patient (802). In the example of FIG. 8, processing circuitry 110 determines a current blood pressure value for the patient (804). Processing circuitry 110 can determine a new blood pressure value of the patient based on a new portion of a signal received from sensing circuitry 141.

In the example of FIG. 8, processing circuitry 110 sets the autoregulation state value associated with the current blood pressure value (806). Processing circuitry 110 can also determine a new autoregulation state value for the patient at the current blood pressure. Processing circuitry 110 can use previously determined values of physiological parameters. Processing circuitry 110 can set the autoregulation state value in the state vector associated with the current blood pressure to the newly determined autoregulation state value.

In the example of FIG. 8, processing circuitry 110 determines whether there are any anomalous values of the plurality of autoregulation state values (808). Responsive to determining that there are no anomalous values, processing circuitry 110 receives new portion(s) of one or more signals from the patient. Processing circuitry 110 then repeats the steps of 804, 806, and 808.

Processing circuitry 110 can identify an autoregulation state value as anomalous based on determining that the autoregulation state value represents an intact autoregulation state, is in a small region of intact values, and is far away from the largest intact region. Processing circuitry 110 can also identify an autoregulation state value as anomalous based on determining that the autoregulation state value represents an impaired autoregulation state, is in a small region of impaired values, and is far away from the largest impaired regions.

Processing circuitry 110 may be configured to identify a small region of state values as a group or cluster of less than a threshold number of nearby state values with the same state value. In examples in which the autoregulation state values are spaced at one millimeter of mercury, the threshold number may be three, five, or ten millimeters of mercury, for example. Processing circuitry 110 may also be configured to identify a small region based on determining that the region is far away from a larger region of the same state values. In examples in which the autoregulation state values are spaced at one millimeter of mercury, processing circuitry 110 can determine that two regions are far away if the two regions are separate by at least five, ten, fifteen, or twenty millimeters of mercury and no autoregulation state values indicating the same state, for example.

One example technique for determining anomalous values is to apply a smoothing function the plurality of autoregulation state values. Processing circuitry 110 may be configured to generate a plurality of smoothed autoregulation state values based on the application of the smoothing function. Processing circuitry 110 can pass the plurality of autoregulation state values through the smoothing function to generate smoothed autoregulation state values. The smoothing function may operate as a moving average, a low-pass filter, or a Gaussian filter to remove outliers in the plurality of autoregulation state values. A Gaussian filter may use a bell-shaped curve to weight the nearby unsmoothed autoregulation state values (e.g., original) in generating a smoothed autoregulation state value. A smoothed autoregulation state value may be equal to a weighted average of the nearby unsmoothed autoregulation state values. Processing circuitry 110 may be configured to determine that an autoregulation state value is anomalous in examples in which the smoothed and unsmoothed autoregulation state values have different values. Using the smoothing function, processing circuitry 110 can remove or modify small regions of anomalous state values.

In some examples, processing circuitry 110 is configured to fit the whole autoregulation state vector, or a portion of the vector, to an expected autoregulation function, to change unknown or anomalous state values to a consistent state value. For the expected autoregulation function, processing circuitry 110 can use a previous morphology of autoregulation state values or a fit of historical patient data, such as historical patient blood pressure value data. The expected autoregulation function may include a lower limit of autoregulation, an upper limit of autoregulation, a set of autoregulation state values representing an intact autoregulation state between the lower limit of autoregulation and the upper limit of autoregulation, and two sets of autoregulation state values representing an impaired autoregulation state, one set below the lower limit of autoregulation and the other set above the upper limit of autoregulation.

In the example of FIG. 8, responsive to determining that there are anomalous values, processing circuitry 110 modifies the anomalous autoregulation state values (810). In examples in which processing circuitry 110 applies a smoothing function to determine an anomalous autoregulation state value, processing circuitry 110 may be configured to set the anomalous autoregulation state value to the smoothed autoregulation state value. Processing circuitry 110 can determine that an autoregulation state value is anomalous using a smoothing function by determining that the unsmoothed and smoothed autoregulation state values associated with a particular blood pressure value are different.

Processing circuitry 110 can also use estimates of the limits of autoregulation to replace anomalous autoregulation state values. In some examples, processing circuitry 110 is configured to replace an autoregulation state value below the lower limit of autoregulation or above the upper limit of autoregulation, where the autoregulation state value represents an intact autoregulation state. Processing circuitry 110 may be configured to replace an autoregulation state value above the lower limit of autoregulation and below the upper limit of autoregulation, where the autoregulation state value represents an impaired autoregulation state.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200, processing circuitry 110, 210, 214, and 216, memories 120 and 220, displays 132 and 232, sensing circuitries 140-142, circuitries 240 and 245, sensing devices 150-152 and 250, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices, such as between devices 100 and 200, processing circuitry 110, 210, 214, and 216, memories 120 and 220, sensing circuitries 140-142, and/or circuitries 240 and 245. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200, processing circuitry 110, 210, 214, and 216, memories 120 and 220, displays 132 and 232, sensing circuitries 140-142, circuitries 240 and 245, sensing devices 150-152 and 250 may be programmed with various forms of software. The one or more processors may be implemented at least in part as, or include, one or more executable applications, application modules, libraries, classes, methods, objects, routines, subroutines, firmware, and/or embedded code, for example.

In examples in which processing circuitry 110 is described herein as determining that a value is less than or equal to another value, processing circuitry 110 may be configured to determine that a value is only less than the other value. Similarly, in examples in which processing circuitry 110 is described herein as determining that a value is less than another value, processing circuitry 110 may be configured to determine that a value is less than or equal to the other value. The same properties may also apply to the terms "greater than" and "greater than or equal to."

Various examples of the disclosure have been described. Any combination of the described systems, operations, or functions is contemplated. These and other examples are within the scope of the following claims.

What is claimed is:

1. A device comprising:
sensing circuitry configured to receive one or more signals from a patient; and
processing circuitry configured to:
derive a plurality of correlation coefficients based on the one or more signals;
determine a plurality of autoregulation state values associated with a plurality of blood pressure values based on the plurality of correlation coefficients, wherein the plurality of autoregulation state values include a first intact autoregulation value associated with a first blood pressure and a first impaired autoregulation value associated with a second blood pressure;
store, in a data structure, the plurality of autoregulation state values and the plurality of blood pressure values, wherein each autoregulation state value of the plurality of autoregulation state values is associated with a corresponding blood pressure value of the plurality of blood pressure values in the data structure;
determine that a first autoregulation state value of the plurality of autoregulation state values is anomalous based on surrounding autoregulation state values in the data structure;
modify the first autoregulation state value in response to determining that the first autoregulation state value is anomalous; and determine an autoregulation status of the patient based on the plurality of autoregulation state values including the modified first autoregulation state value.

2. The device of claim 1, wherein the processing circuitry is configured to determine that the first autoregulation state value is anomalous at least in part by:
identifying a set of intact autoregulation state values of the plurality of autoregulation state values, each of the intact autoregulation state values of the set representing an intact autoregulation state;
determining that the first autoregulation state value represents an intact autoregulation state; and
determining that a difference between a blood pressure value associated with the first autoregulation state value and each of a set of blood pressure values associated with the set of intact autoregulation state values is greater than a threshold value.

3. The method of claim 1, wherein the processing circuitry is configured to determine that the first autoregulation state value is anomalous at least in part by:
determining a limit of autoregulation based on the plurality of autoregulation state values;
determining that the first autoregulation state value represents an intact autoregulation state; and
determining that the first autoregulation state value is outside of the limit of autoregulation.

4. The device of claim 1, wherein the processing circuitry is configured to determine that the first autoregulation state value is anomalous at least in part by:
identifying a first set of impaired autoregulation state values of the plurality of autoregulation state values, each of the impaired autoregulation state values of the set representing an impaired autoregulation state;
determining that the first autoregulation state value represents an impaired autoregulation state; and
determining that a difference between a blood pressure value associated with the first autoregulation state value and each of a set of blood pressure values associated with the set of impaired autoregulation state values is greater than a threshold value.

5. The device of claim 1, wherein determining that the first autoregulation state value is anomalous at least in part by:
determining a limit of autoregulation based on the plurality of autoregulation state values;
determining that the first autoregulation state value represents an impaired autoregulation state; and
determining that the first autoregulation state value is inside of the limit of autoregulation.

6. The device of 1, wherein the processing circuitry is configured to determine that the first autoregulation state value is anomalous at least in part by:
determining that the first autoregulation state value represents an uncategorized autoregulation state; and
determining that a first set of autoregulation state values of the plurality of autoregulation state values has a categorized autoregulation value, the categorized autoregulation value representing a categorized autoregulation state, wherein the categorized autoregulation value includes a second intact autoregulation value or a second impaired autoregulation value, and wherein the first set of autoregulation state values is associated with blood pressure values that are higher than a blood pressure value associated with the first autoregulation state value; and
determining that a second set of autoregulation state values of the plurality of autoregulation state values has the categorized autoregulation value, wherein the second set of autoregulation state values is associated with blood pressure values that are lower than a blood pressure value associated with the first autoregulation state value,
wherein the processing circuitry is configured to modify the first autoregulation state value at least in part by setting the first autoregulation state value to the categorized value.

7. The device of claim 1, wherein the first autoregulation state value is associated with a third blood pressure value, wherein the processing circuitry is configured to determine that the first autoregulation state value is anomalous at least in part by:
applying a smoothing function to the plurality of autoregulation state values to generate a plurality of smoothed autoregulation state values; and
determining that a first smoothed autoregulation state value of the plurality of smoothed autoregulation state values and the first autoregulation state value have different values, wherein the first smoothed autoregulation state value is associated with the third blood pressure value,
wherein the processing circuitry is configured to modify the first autoregulation state value at least in part by setting the first autoregulation state value to the first smoothed autoregulation state value in response to determining that the first smoothed autoregulation state value and the first autoregulation state value have different values.

8. The device of claim 1, wherein the first autoregulation state value is associated with a third blood pressure value, and wherein the processing circuitry is configured to:
determine a confidence metric for autoregulation state values associated with blood pressure values within a threshold value from the third blood pressure value, wherein the autoregulation state values associated with the blood pressure values within the threshold value from the third blood pressure value have a predominant autoregulation value; and
determine that the confidence metric is greater than a threshold confidence level,
wherein the processing circuitry is configured to modify the first autoregulation state value at least in part by setting the first autoregulation state value to the predominant autoregulation value in response to determining that the confidence metric is greater than the threshold confidence level.

9. The device of claim 1, wherein the processing circuitry is further configured to:
store an unmodified value of the first autoregulation state value; and
determine new autoregulation values for the plurality of autoregulation state values after modifying the first autoregulation state value and based on the unmodified value of the first autoregulation state value.

10. The device of claim 1, wherein the processing circuitry is further configured to apply an expected autoregulation function to the plurality of autoregulation state values to generate a modified plurality of autoregulation state values, the expected autoregulation function including:
a lower limit of autoregulation;
an upper limit of autoregulation;
a set of intact autoregulation state values between the lower limit of autoregulation and the upper limit of autoregulation;

a first set of impaired autoregulation state values associated with blood pressure values less than the lower limit of autoregulation; and a second set of impaired autoregulation state values associated with blood pressure values greater than the upper limit of autoregulation.

11. The device of claim 1, wherein the processing circuitry is further configured to:

determine a current blood pressure value for the patient based on the one or more signals; and set a second autoregulation state value of the plurality of autoregulation state values, wherein the second autoregulation state value is associated with the current blood pressure value.

12. The device of claim 1, wherein the processing circuitry is further configured to output for display data indicative of the autoregulation status of the patient.

13. The device of claim 12, wherein the processing circuitry is further configured to:

output for display first data indicative of a first color for the modified first autoregulation state value in response to determining that the modified first autoregulation state value represents an intact autoregulation state; and output for display second data indicative of a second color for the modified first autoregulation state value in response to determining that the modified first autoregulation state value represents an impaired autoregulation state.

14. A method comprising:

receiving, by processing circuitry, one or more signals from a patient;

deriving a plurality of correlation coefficients based on the one or more signals;

determining, by the processing circuitry, a plurality of autoregulation state values associated with a plurality of blood pressure values based on the plurality of correlation coefficients, wherein the plurality of autoregulation state values include a first intact autoregulation value associated with a first blood pressure and a first impaired autoregulation value associated with a second blood pressure;

storing, in a data structure, the plurality of autoregulation state values and the plurality of blood pressure values, wherein each autoregulation state value of the plurality of autoregulation state values is associated with a corresponding blood pressure value of the plurality of blood pressure values in the data structure;

determining, by the processing circuitry, that a first autoregulation state value of the plurality of autoregulation state values is anomalous based on surrounding autoregulation state values of the plurality of autoregulation state values in the data structure;

modifying, by the processing circuitry, the first autoregulation state value in response to determining that the first autoregulation state value is anomalous; and determining, by the processing circuitry, an autoregulation status of the patient based on the plurality of autoregulation state values including the modified first autoregulation state value.

15. The method of claim 14, wherein determining that the first autoregulation state value is anomalous comprises:

determining a limit of autoregulation based on the plurality of autoregulation state values;

determining that the first autoregulation state value represents an intact autoregulation state; and determining that the first autoregulation state value is outside of the limit of autoregulation.

16. The method of claim 14, wherein determining that the first autoregulation state value is anomalous comprises:

determining a limit of autoregulation based on the plurality of autoregulation state values;

determining that the first autoregulation state value represents an impaired autoregulation state; and determining that the first autoregulation state value is inside of the limit of autoregulation.

17. The method of 14, wherein the first autoregulation state value is associated with a third blood pressure value, wherein determining that the first autoregulation state value is anomalous comprises:

applying a smoothing function to the plurality of autoregulation state values to generate a plurality of smoothed autoregulation state values; and determining that a first smoothed autoregulation state value of the plurality of smoothed autoregulation state values and the first autoregulation state value have different values, wherein the first smoothed autoregulation state value is associated with the third blood pressure value, wherein modifying the first autoregulation state value comprises setting the first autoregulation state value to the first smoothed autoregulation state value in response to determining that the first smoothed autoregulation state value and the first autoregulation state value have different values.

18. A device comprising a computer-readable medium having executable instructions stored thereon, configured to be executable by processing circuitry for causing the processing circuitry to:

receive one or more signals from a patient;

derive a plurality of correlation coefficients based on the one or more signals;

determine a plurality of autoregulation state values associated with a plurality of blood pressure values based on the plurality of correlation coefficients, wherein the plurality of autoregulation state values include a first intact autoregulation value associated with a first blood pressure and a first impaired autoregulation value associated with a second blood pressure;

store, in a data structure, the plurality of autoregulation state values and the plurality of blood pressure values, wherein each autoregulation state value of the plurality of autoregulation state values is associated with a corresponding blood pressure value of the plurality of blood pressure values in the data structure;

determine that a first autoregulation state value of the plurality of autoregulation state values is anomalous based on surrounding autoregulation state values of the plurality of autoregulation state values in the data structure;

modify the first autoregulation state value in response to determining that the first autoregulation state value is anomalous; and determine an autoregulation status of the patient based on the plurality of autoregulation state values including the modified first autoregulation state value.

19. The device of claim 18, wherein the instructions to determine that the first autoregulation state value is anomalous comprise instructions to:

determine a limit of autoregulation based on the plurality of autoregulation state values;

determine that the first autoregulation state value represents an intact autoregulation state; and determine that the first autoregulation state value is outside of the limit of autoregulation.

20. The device of claim 18, wherein the instructions to determine that the first autoregulation state value is anomalous comprise instructions to:
- determine a limit of autoregulation based on the plurality of autoregulation state values;
- determine that the first autoregulation state value represents an impaired autoregulation state; and
- determine that the first autoregulation state value is inside of the limit of autoregulation.

* * * * *